US012496211B2

(12) United States Patent
Reuter

(10) Patent No.: US 12,496,211 B2
(45) Date of Patent: Dec. 16, 2025

(54) LIMB SHIELDING DEVICES

(71) Applicant: Moritz Emil Reuter, London (GB)

(72) Inventor: Moritz Emil Reuter, London (GB)

(*) Notice: Subject to any disclaimer, the term of this patent is extended or adjusted under 35 U.S.C. 154(b) by 276 days.

(21) Appl. No.: 17/797,844

(22) PCT Filed: Feb. 5, 2021

(86) PCT No.: PCT/GB2021/050259
§ 371 (c)(1),
(2) Date: Aug. 5, 2022

(87) PCT Pub. No.: WO2021/156627
PCT Pub. Date: Aug. 12, 2021

(65) Prior Publication Data

US 2023/0079084 A1 Mar. 16, 2023

(30) Foreign Application Priority Data

Feb. 6, 2020 (GB) ...................................... 2001622

(51) Int. Cl.
*A61F 5/37* (2006.01)

(52) U.S. Cl.
CPC ...................................... *A61F 5/37* (2013.01)

(58) Field of Classification Search
CPC ........ A61F 5/37; A61F 5/3723; A61F 5/3746; A41D 13/08; A41D 13/05; A41D 13/00; A63B 71/08
See application file for complete search history.

(56) References Cited

U.S. PATENT DOCUMENTS

| | | | |
|---|---|---|---|
| 824,174 | A | 6/1906 | Clark et al. |
| 1,397,624 | A | 11/1921 | Epling |

(Continued)

FOREIGN PATENT DOCUMENTS

| | | |
|---|---|---|
| CN | 202010226 | 10/2011 |
| CN | 102657566 | 9/2012 |

(Continued)

OTHER PUBLICATIONS

Official Action with English Translation for Japan Patent Application No. 2022-548182, dated Dec. 10, 2024, 6 pages.

(Continued)

*Primary Examiner* — Tarla R Patel
(74) *Attorney, Agent, or Firm* — Sheridan Ross P.C.

(57) ABSTRACT

The present invention is directed towards a limb shielding device, for shielding a user's hand. The device comprises a shielding member, configured to shield at least part of a user's limb, including the hand, which comprises an opening arranged at a proximal end of the shielding member and dimensioned to allow a user's limb to be inserted into the shielding member. The device also comprises a means for restricting the opening relative to the user's limb such that once the limb is inserted and the opening is restricted relative to the user's limb, the limb cannot be retracted through the opening. The device further comprises a closure member capable of being moved, by the user's hand within the shielding member, into a closed position such that at least part of the limb is constrained within the shielding member, and a locking arrangement for securing the closure member in the closed position.

20 Claims, 14 Drawing Sheets

(56) References Cited

U.S. PATENT DOCUMENTS

| | | | | |
|---|---|---|---|---|
| 2,043,153 | A | 6/1936 | Cox | |
| 2,728,914 | A | 1/1956 | Mercur | |
| 3,415,244 | A * | 12/1968 | Block | A61F 5/37 2/16 |
| 4,887,616 | A * | 12/1989 | Baijnath | A61F 5/05866 128/879 |
| 5,279,574 | A * | 1/1994 | Forren | A61M 25/02 604/179 |
| 5,769,809 | A * | 6/1998 | Witzel | A61F 2/7812 623/32 |
| 6,276,364 | B1 * | 8/2001 | Warner | A61M 25/02 128/846 |
| 6,283,126 | B1 * | 9/2001 | Jessen | A61F 15/004 128/878 |
| 6,328,706 | B1 | 12/2001 | Yattavong | |
| 6,895,971 | B1 | 5/2005 | Evans | |
| 7,942,152 | B1 * | 5/2011 | Foster | A61F 5/37 119/770 |
| 10,786,405 | B2 * | 9/2020 | Fujii | A61F 13/041 |
| 10,918,836 | B2 * | 2/2021 | Jutras | A61M 25/02 |
| 11,666,107 | B2 * | 6/2023 | Potnis | A41D 19/0048 2/16 |
| 11,833,324 | B2 * | 12/2023 | Brunner | A61M 5/158 |
| 2011/0289642 | A1 | 12/2011 | Pena | |
| 2017/0049603 | A1 * | 2/2017 | Lambert | A61F 5/05866 |

FOREIGN PATENT DOCUMENTS

| | | | |
|---|---|---|---|
| CN | 202761510 | 3/2013 | |
| CN | 208741240 | 4/2019 | |
| JP | H11-4843 | 1/1999 | |
| JP | 2002-172126 | 6/2002 | |
| JP | 2007-082457 | 4/2007 | |
| JP | 2009-213522 | 9/2009 | |
| JP | 3157912 | 3/2010 | |
| KR | 10-2010-0038347 | 4/2010 | |
| KR | 10-1499192 | 3/2015 | |
| KR | 10-2016-0134335 | 11/2016 | |
| WO | WO 2007/111920 | 10/2007 | |
| WO | WO-2007111920 A2 * | 10/2007 | A61F 5/0118 |

OTHER PUBLICATIONS

International Search Report and Written Opinion for International (PCT) Patent Application No. PCT/GB2021/050259, dated May 6, 2021, 9 pages.

* cited by examiner

LIMB SHIELDING DEVICES

CROSS REFERENCE TO RELATED APPLICATIONS

This application is a national stage application under 35 U.S.C. 371 and claims the benefit of PCT Application No. PCT/GB2021/050259 having an international filing date of 5 Feb. 2021, which designated the United States, which PCT application claimed the benefit of Great Britain Application No. 2001622.6 filed 6 Feb. 2020, the disclosures of each of which are incorporated herein by reference in their entireties.

FIELD OF THE INVENTION

The present invention relates to limb shielding devices, particularly to limb shielding devices for shielding a user's hand.

BACKGROUND

The limbs of humans, and animals, often require shielding for a number of different reasons. For example, when a limb has been injured, it is often beneficial to shield the limb to prevent further damage to the limb. Limbs are also often shielded in order to prevent the limb from accessing and causing harm to e.g. another part of the body. For example, in the case of a person who has atopic dermatitis (eczema), the person may use a limb shield designed to stop their hand from being used to scratch their body. Taking the case of eczema as an example, conventional solutions include soft gloves or garments with integrated mittens. However, such solutions only provide superficial protection as they still permit scratching through the layer of fabric covering the fingers. Additionally, the act of rubbing the fabric against the skin, rather than scratching directly, may peel off the outer epidermis layer (excoriation), leading to raw and open skin wounds.

Not only are the gloves and mittens of the type described above ineffective at preventing scratching, such gloves and garments are often unwittingly removed during sleep and may be insufficiently breathable, making them unhygienic and uncomfortably hot.

Other solutions for shielding a user's hand include shields formed from a flexible but stiff material designed to extend around a user's hand. Such shields often include a wrist wrap at one end thereof for securing the shield to the user wrist or arm. Due to the inherent problem of at least one hand being shielded by the shield, and thus unable to perform any meaningful function, such shields are difficult for a user to attach and detach themselves and often require a third party to attach and detach the shield.

The present invention aims to address or at least mitigate some of the problems outlined above.

SUMMARY

When viewed from a first aspect, the present invention provides a limb shielding device, for shielding a user's hand, comprising: a shielding member, configured to shield at least part of a user's limb, including the hand, comprising an opening arranged at a proximal end of the shielding member and dimensioned to allow a user's limb to be inserted into the shielding member; a means for restricting the opening relative to the user's limb such that once the limb is inserted and the opening is restricted relative to the user's limb, the limb cannot be retracted through the opening; a closure member capable of being moved, by the user's hand within the shielding member, into a closed position such that at least part of the limb is constrained within the shielding member; and a locking arrangement for securing the closure member in the closed position.

Thus, a limb shielding device is provided which a user can attach, and optionally detach, themselves, without requiring any further assistance from a third party. This may be achieved using the same hand which is shielded by the limb shielding device. A user may, for example, first insert their hand through the opening in the shielding member, and then apply the means for restricting the opening relative to the user's limb such that their hand cannot be retracted through the opening. They may then move the closure member into a closed position and operate the locking arrangement such that the closure member is held in the closed position. The locking arrangement may be operable by the hand within the shielding member. Accordingly, with this arrangement the user is not reliant on a third party for attaching the limb shielding device. The ability to self-attach and self-detach the limb shielding device may open up the number of applications of the limb shielding device as it may, for example, be used in the home, where assistance from third parties may not be feasible or practical.

The limb shielding device may be used to protect the hand contained within the shielding device. For example, the limb shielding device may be used to protect the hand within the shielding device from physical harm or from exposure to pathogens through contact with contaminated surfaces. For example, the limb shielding device may protect the hand within the device from viruses, for example coronavirus. Additionally or alternatively, the limb shielding device may be used to shield the hand within the shielding device from accessing, for example, other parts of the user's body. For example, the limb shielding device may be used to physically prevent the user from using their hands and fingers to harm themselves or others in any conceivable way (e.g. scratching; punching; pulling intravenous (IV) tubes; wrist-cutting; thumb-sucking; nail-biting; compulsive binge-eating; substance abuse or addiction to drugs, alcohol, tobacco etc.). As a further example, the limb shielding device may be used to physically prevent the user from using their hands and fingers to transmit pathogens to others through direct or indirect contact, or to spread pathogens to other parts of the user's body, such as mucous membranes on the user's face, thereby reducing the risk of causing an infection, for example COVID-19. This example may be particularly relevant in the case of elderly, immunocompromised or other clinically vulnerable users. This example may also be particularly relevant in environments with high risk of coming into contact with pathogens, for example during a pandemic.

The limb shielding device may be particularly advantageous for use in physically preventing scratching in patients with atopic dermatitis (eczema) or any other condition associated with chronic refractory pruritus (e.g. contact dermatitis, psoriasis, urticaria, xerosis, lichen simplex chronicus, lichen planus, prurigo nodularis, *Pityriasis rosea*, Hodgkin's disease, HIV, scabies, chronic hepatic and renal disease etc.). Chronic pruritus is estimated to afflict approximately 15% of the population and can severely impair quality of life and emotional well-being. The shielding device may be an adjunct treatment tool which empowers patients to better control their scratching. The ability to self-attach and self-detach the limb shielding device makes it particularly suitable for applications where a user themselves may want to have control over wearing the limb shielding device without necessarily requiring assistance from others.

The limb shielding device may be especially useful during sleep when the intensity of the itch is often more severe and when the act of scratching becomes subconscious and involuntary. The limb shielding device may be dimensioned such that a patient wearing the device maintains full freedom of arm movement allowing them to still go through the motions of scratching, but without actually causing any skin damage. Preventing scratching in this way gives the skin respite, aids the healing process and improves the patient's chances of ultimately breaking the vicious itch-scratch cycle. The limb shielding device may also be useful during periods of remission by keeping flares in check at their first sign of onset and preventing any relapses from causing further exacerbation.

The means for restricting the opening may comprise a restriction element, separate from the shielding member, configured to attach around a user's limb such that an outer dimension of the restriction element is greater than the opening, thereby restricting the opening relative to the user's limb. The restriction element, when attached to the limb, may be sized to enable it to be moved within the shielding member. Whilst the restriction element does not directly restrict the size of the opening itself, it acts to increase the effective outermost dimension of the user's limb and thus acts to effectively restrict the size of the opening relative to the user's limb. Such a restriction element may provide a simple means for restricting the opening relative to the user's limb. Additionally, such a restriction element may advantageously allow the limb shielding device to move more freely with respect to the user's limb. For example, it may allow lateral, longitudinal and rotational movement relative to the user's limb. This freedom of movement may provide increased comfort for the user and potentially increase the period of time for which the user can comfortably wear the limb shielding device. This freedom of movement may be achieved through appropriate sizing of the shielding member, the restriction element, the opening and the position of the closure member within the shielding member. The distance between the closure member in its closed position and the opening may define the longitudinal degree of freedom within the shielding device. Additionally, by not fixing the limb shielding device in position and allowing movement through provision of the restriction element, the blood flow to the user's hand may not, necessarily, be restricted.

Of course, any other suitable means for restricting the opening may be provided which can be operated by the hand which is shielded by the limb shielding device. For example, the means for restricting the opening may comprise a mechanical iris which is operable from within the limb shielding device.

The shielding member itself may have any suitable dimension, and may be dimensioned to allow the user to move their hand within the shielding member, for example to flex their fingers or form a fist. The shielding device may be dimensioned so as not to restrict movement of the user's arm. For example, it may be dimensioned such that it does not extend past the user's elbow. This may allow the user to bend their arm. This freedom of movement may improve the comfort of the shielding device which may mean that the user is more likely to wear the shielding device, and less likely to prematurely remove it. In the case where the limb shielding device is used to prevent the user from agitating their eczema, this may mean that the user wears the device more and for longer periods, thus minimising the amount of scratching.

In addition to the locking arrangement being operable to secure the closure member in the closed position, the locking arrangement may also be configured such that the user can operate the locking arrangement to release the closure member from the closed position and allow the user to move the closure member into an open position. This may therefore allow the user to self-detach the device as well as self-attach. The user may therefore be able to remove the shielding device without external assistance, thus giving the user full control over the wearing of the limb shielding device. This may allow the user to remove the limb shielding device in the case of an emergency, and thus a user wearing the device may require less supervision. Any suitable locking arrangement may be provided for this purpose.

The locking arrangement may be configured to be capable of being released following a predetermined operation performed by the limb within the shielding member, and wherein the closure member is arranged such that it can be moved from the closed position to an open position by the limb within the shielding member. The predetermined operation may be any operation which requires a conscious effort and which is difficult to perform accidentally or subconsciously. The requirement for a user to perform a predetermined operation may thus intentionally complicate the release of the locking arrangement for the user and thus provide a barrier to removal. It may therefore mean that the user has to consciously decide to release the locking arrangement and perform the appropriate predetermined operation. This arrangement may, for example, prevent the user from being able to remove the shielding device subconsciously during their sleep. The predetermined operation may be any suitable operation.

The locking arrangement may comprise a threaded portion on the closure member and a corresponding threaded portion on the shielding member for engagement with one another. When the threaded portions are fully engaged with one another, in order to release the closure member the user would have to perform a predetermined operation comprising rotation of the closure member relative to the shielding member. This may be difficult for a user to perform subconsciously and thus may require them to actively decide to remove the shielding device and perform the predetermined operation. The threaded portion and corresponding threaded portion may each comprise at least half a rotation, preferably one full rotation, of thread. Accordingly, a user would have to rotate the closure member and the shielding member through at least 180 degrees relative to one another before the locking arrangement can be overcome. This amount of rotation may thus provide a barrier to easy detachment and thus may improve compliance in wearing the shielding device. Of course, more rotations of thread may be provided, thereby requiring a number of rotations of the closure member relative to the shielding member.

The locking arrangement may comprise a snap fit arrangement configured to secure the closure member in the closed position. Such an arrangement may allow the closure member to be easily moved into, and secured in, the closed position. This may increase the speed with which the shielding device can be attached to a user. With regard to release, it may be necessary for a user to apply a force to one or more snap fit members simultaneously in order to release the locking arrangement and thus allow movement of the closure member into an open position. The operation of, for example, multiple snap-fit members may thus constitute a predetermined operation which would make removal of the shielding device more difficult for the user. Any suitable snap fit arrangement may be used.

The locking arrangement may comprise at least one radially extending element on one of the closure member or shielding member and at least one female receiving portion, for receiving the radially extending element, on the other of the closure member or shielding member. Such an arrangement may thus provide, for example, a bayonet type fitting. In such an arrangement, it may be necessary to move the closure member both rotationally and longitudinally relative to the shielding member in order to move it into a closed position and also out of the closed position. This movement may thus constitute a predetermined operation which a user must perform in order to release the locking arrangement. The multiple directions of movement may complicate the operation required by the user making it harder for them to subconsciously or accidentally remove the shielding device. The locking arrangement may comprise a bayonet-type fitting or a Storz connector.

The locking arrangement may comprise a locking member arranged to be capable of being driven into a locking position in which the locking member secures the closure member in the closed position. The locking arrangement may further include an electric motor configured to drive the locking member, for example into and out of a locked position.

In another alternative, the locking arrangement may comprise an electromagnetic locking arrangement. Such an electromagnetic locking arrangement may be configured to drive the locking member into and out of a locked position. In either of the variations described above in which the locking arrangement is electronically controlled, e.g. through an electric motor or through an electromagnetic locking arrangement, the locking arrangement may further comprise a switching arrangement within the shield which the user must operate in order to operate the electromagnetic locking arrangement or the electric motor. The switching arrangement may determine the predetermined operation which a user has to perform in order to release the locking arrangement. Through appropriate design of the switching arrangement, it may be possible to ensure that the user has to employ a sustained effort in order to release the locking arrangement. For example, this may require the pressing of buttons in a certain sequence. Any suitable means may be provided to achieve this purpose.

The shielding device may comprise a further locking arrangement operable from an outside of the shielding member. Any suitable further locking arrangement may be provided. For example, the further locking arrangement may comprise a latching arrangement which secures the closure member in the closed position. Accordingly, with such a further locking arrangement, the shielding device may be secured to the user in a manner in which the user cannot release the shielding device with the hand within the shielding member. This may be useful if a third party, e.g. a caregiver, wants to have a level of control over when the user can remove the shielding device. Once the further locking arrangement has been released on an outside of the shielding member, the locking arrangement may be operated by the hand within the shielding member.

The closure member and shielding member may be provided by separable components. For example, in the case of the threaded closure member and shielding member, these two parts may separate from one another. The closure member may alternatively be provided by a sliding member which slides relative to the shielding member into a closed position, and which does not require rotation to secure it in place. For example, the closure member may be configured to slide within at least one groove within the shielding member. Any suitable locking arrangement may be provided to secure the sliding closure member in position. For example, at least one snap-fit arrangement may secure the closure member in its closed position.

In another alternative, the closure member may be pivotally mounted to the shielding member. In this case, whilst they are separate functional parts, the closure member may be attached to the shielding member. This may make it easier for the user to operate the closure member as the closure member is always mounted to the shielding member and does not require the user to separately pick it up. Such a pivotally mounted closure member may comprise a snap-fit arrangement at one end thereof for cooperating with the shielding member to secure the closure member in a closed position.

The closure member may comprise a hand grip for use in moving the closure member relative to the shielding member. The hand grip may allow the user to more easily operate the closure member. For example, the hand grip may allow the user to pull and/or twist the closure member relative to the shielding member. The hand grip itself may constrain the user's hand within the shielding device, i.e. it may act to prevent the user's hand from passing through a distal end of the shielding member. For example, the hand grip may be dimensioned to prevent the hand from passing through the end of the shielding device. However, this is not essential and the hand grip may simply form part of the closure member but not contribute to restricting the hand within the shielding member. The hand grip may take any suitable form. For example, the hand grip may be in the form of a rod-shaped bar suitable for gripping by the user's hand. Alternatively, the hand grip may be provided by other means, for example in the form of a circular ring. The hand grip may advantageously provide an internal feature which the user can grip onto which may provide a distraction for the user, for example a distraction from their itch in the case of an eczema sufferer.

The closure member, at least when in the closed position, may be contained within an outer wall of the shielding member. This may advantageously mean that an outside of the shielding device may be formed from a single piece of smooth material. In other words, there may not be any discontinuity on an outer surface of the shielding member, which may otherwise be formed at a joint between the closure member and the shielding member. This may minimise the number of surfaces on the shielding device which can be used for scratching. However, this is of course not essential, and the closure member may simply abut against an end of the shielding member. In this instance, the shielding member and the closure may be shaped such that the joint formed therebetween is as smooth as possible. For example, this may be achieved by rounding the portions of the closure member and the shielding member which abut against one another.

The restriction element functioning as a means for restricting the opening, and allowing movement of the user's limb relative to the shielding device is novel and inventive in its own right, and thus, when viewed from a further aspect, the present invention provides a limb shielding device comprising: a shielding member, configured to shield at least part of a user's limb, comprising an opening dimensioned to allow a user's limb to be inserted into the shielding member; and a restriction element, separate from the shielding member, configured to attach around a user's limb such that an outer dimension of the restriction element is greater than the opening so that the user's limb cannot be retracted through the opening and such that the restriction element when attached to the limb may be moved within the shielding member.

Such a limb shielding device may afford the same advantages as those described above with respect to the restriction element, namely it may permit at least a small amount of movement of the shielding device relative to the user's limb which may increase the relative comfort of the shielding device. The limb shielding device according to this aspect need not necessarily be limited to use with a human hand, and instead may find use in shielding any limb, which may be the limb of a human or an animal. Whilst it may still be possible for the user to self-attach the shielding member, in embodiments of this further aspect of the invention, the shielding member may be attached to the limb by a third party, e.g. a caregiver.

The restriction element and the opening may be dimensioned to allow at least one of lateral, rotational and longitudinal movement of the user's limb relative to the shielding member when the limb is within the shielding member. The shielding member may not cover an entire limb, and may instead be used to cover part of a user's limb.

The limb shielding device of this further aspect may comprise a closure member arranged to permanently prevent a user's limb from passing through the distal end of the device.

The following are features which may be applied to embodiments of either the first or further aspect of the invention.

Where provided, the closure member may define at least one aperture extending through the closure member. The at least one aperture may allow stimulation of the user's hand within the shielding device by external means without removing the device. Additionally, the at least one aperture may allow limited functionality of a user's hands, e.g. allowing them to operate a door knob. The at least one aperture may function as a vent aperture. This airflow may increase the comfort of the shielding device for the user. The aperture may be in the closure member itself. Alternatively, the closure member may only partially close the shielding member, and thus the portion of an opening which the closure member does not close may form the at least one vent aperture. For example, in the case of the shielding member having a circular cross section with a hinged closure member in the form of a bar, the aperture may be formed either side of the bar between the bar and the inside walls of the shielding member.

The restriction element may comprise a fastening element configured to secure the restriction element in place around a user's limb. The fastening element may be operated by a user once the restriction element has been attached to their limb, and the fastening element may secure the restriction element in a manner which prevents removal of the restriction element from the user's limb without release of the fastening element. The fastening element may, for example, comprise a strap. The strap may secure the restriction element in any suitable manner. For example, the strap may comprise at least one of: Velcro, a press stud or a buckle, configured to hold the strap in position in which the restriction element is secured in place.

Where provided, the restriction element may have an adjustable size. The restriction element may comprise any suitable means for allowing adjustment of its size. For example, adjustment may be achieved through an adjustable strap. This may allow the restriction element to be suitable for a number of different users and/or limbs. Such a strap may also function as a fastening element, as described above.

It may be possible for a user to pass their limb through an opening in the restriction element without opening the restriction element. For example, the restriction element may be partially expandable to permit this form of operation. This may be achieved by the restriction element being made from an expandable, e.g. elastic, material. However, the restriction element may be configured such that it can be opened for receiving a user's limb and closed for securing around the user's limb. This may allow the restriction element to be more easily attached to the user's limb.

The restriction element may be at least partially deformable. This may provide increased comfort for the user as it may effectively provide a cushion between the limb and the shielding member. The restriction element may be deformable such that it is comfortable for the user, but sufficiently rigid that it cannot be forced through the opening on the shielding member thereby providing its function of preventing the limb from being retracted through the opening. The restriction element may, for example, be filled with a deformable material. The deformable material may comprise a hollow fibre filling or foam. In addition, or alternatively, the restriction element may be filled with a plurality of pellets which contribute to the deformability of the restriction element.

The restriction element may be inflatable. This may advantageously mean that the restriction element can also be constrained within the shielding member and simply be inflated around a user's limb when the limb is inserted into the shielding member. An inflatable restriction element may also be comfortable for a user as it may be at least partially deformable.

The limb shielding device may further comprise a vent aperture at the proximal end of the shielding member. This may further promote airflow into the shielding device, thereby improving comfort for the user. When combined with embodiments in which there are further vent apertures in the shielding device, this additional vent aperture may help to promote an airflow through the device, thereby improving comfort. Additionally, as the proximal end of the shielding member may frequently come into contact with part of the user's limb, e.g. their arm or wrist, a vent aperture at this end may increase air flow to the portion of the shielding device which is most frequently in contact with the user's limb. This may improve comfort and increase the period of time for which the limb shielding device can be comfortably worn.

At least the shielding member may be transparent. This may advantageously allow the user or a caregiver to visually inspect and monitor the user's limb without having to remove the shielding device. Of course, other parts of the shielding device may also be transparent, for example the closure member.

At least the shielding member may be formed of a sheet of material which comprises rounded proximal and distal ends. Through the use of a sheet material, the weight of the shielding member, and thus the shielding device, may be minimised. This may make the shielding device more comfortable for the user. The rounded proximal and distal ends may prevent the user from being able to use the ends of the shielding device as a scratching means. Additionally, the rounded proximal and distal ends may ensure that the sheet material is not uncomfortable for the user. The rounded proximal and distal ends may be achieved in any suitable manner. For example, the proximal and distal ends may be moulded such that they are rounded. Alternatively, or in addition, a rounded element may be attached to the proximal and distal ends. The rounded element may be made from the same material as the shielding member. However, it may be possible to make the rounded element from a different material. The shielding member may comprise foam arranged on an inside surface thereof. This may improve the comfort of the shielding device for the user.

At least the shielding member may be formed from an at least semi-rigid material. Such a material may protect the limb within the device and also prevent the user from being able to use the limb for other purposes, e.g. for scratching. The at least semi-rigid material may be partially flexible and deformable but sufficiently rigid that the user cannot perform any function through the shielding member, e.g. preventing the user from performing a scratching action. The shielding member may be formed from a rigid material. The shielding member may, for example be formed from plastic, e.g. a rigid plastic foam. The use of plastic may advantageously provide a surface which is cool to the touch and soothing for inflamed skin. Of course, other parts of the limb shielding device may also be made from plastic.

The limb shielding device may further comprise a means to determine the length of time the limb shielding device has been worn by the user. This may allow the user, or a caregiver, to more accurately monitor the wearing of the limb shielding device. In certain applications where compliance is important, this may provide useful additional information for the user or for the caregiver. Any suitable means may be provided for this purpose. For example, the means to determine the length of time the limb shielding device has been worn may comprise at least one of a heat sensor, opto-electronic sensor, and accelerometer. An accelerometer may indirectly measure the wear time, whilst also measuring the amount of movement and agitation of the user, for example whilst a user is sleeping. The shielding device may be configured to provide an alert based on the time worn by the user, for example an alert to a caregiver. This may be achieved through any suitable means and the alert may be provided on the shielding device or on another device, e.g. a mobile device.

Alternative means may be provided for monitoring wearing compliance. For example, the shielding device may be provided with a breakable element which is broken upon removal of the shielding device. This may be in form of a string or other suitable element. The shielding device may comprise a marking which is difficult to achieve realignment of when the shielding device is removed and reattached. This misalignment may allow a caregiver to easily determine that the shielding device has been removed.

The shielding member may comprise a plurality of apertures extending therethrough. This may increase the airflow into the shielding member. However, the shielding member may comprise a smooth outer surface. Such an arrangement may advantageously prevent the shielding member from being used by a user to scratch as the smooth surface will not be suitable for performing a scratching action. An inside of the shielding member may be smooth so as to provide comfort for the limb within the shielding member.

To allow a better understanding, embodiments of the present invention will now be described by way of non-limitative examples with reference to the accompanying drawings, in which.

DETAILED DESCRIPTION

Figure 1:
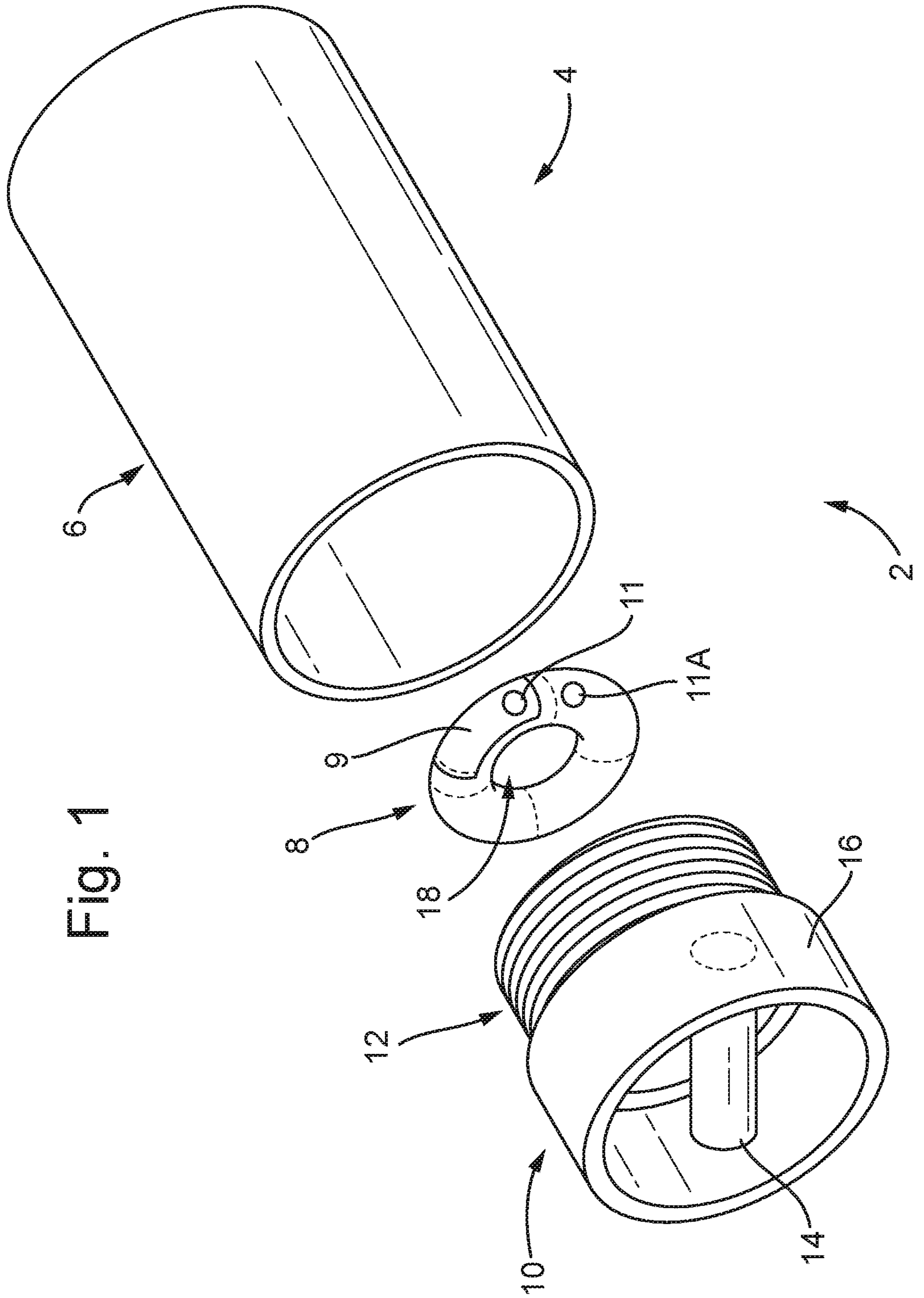
FIG. 1 is an exploded view of a limb shielding device.

FIG. 1 shows a perspective view of a limb shielding device 2, hereinafter referred to as a device 2, for shielding a user's hand in accordance with an embodiment of the present invention. The device 2 comprises a shielding member 4 configured to shield at least part of a user's limb, including the hand. The shielding member 4 is formed by a cylindrical tube 6. Whilst in the embodiment shown the shielding member 4 is formed by a cylindrical tube 6, this is not essential, and the shielding member 4 may have any suitable shape depending on its particular application. For example, the cylindrical tube 6, of the shielding member 4, may have a frustoconical shape. The cylindrical tube 6 may not necessarily have a circular cross section and instead the cylindrical tube 6 may have any other shaped cross section, e.g. elliptical. As shown in FIG. 1, the shielding member 4 may be formed from a sheet material, which may mean that the weight of the device 2 is kept to a minimum. The shielding member 4 may be formed from an at least semi-rigid material. Such a material may be partially flexible and deformable but sufficiently rigid that it is not possible for the user to perform actions through the shielding member 4, e.g. so as to prevent them from scratching. The cylindrical tube 6 may, for example, have a wall thickness in the range of 0.3 mm to 3 mm.

The device 2 comprises restriction element 8 which is separate from the shielding member 4. The restriction element 8 has a toroidal shape. Whilst in the embodiment shown the restriction element 8 has a toroidal shape, the restriction element 8 may have any other suitable form and need not necessarily be toroidal in shape, for example it may be formed as a hollow cylinder. The restriction element 8 comprises a hole 18 through which a user's limb may be inserted. The restriction element 8 may be deformable, and at least partially expandable. This may allow the user to push their hand through the opening 18 in order to attach the restriction element 8 to their limb. The restriction element 8 may comprise a fastening element 9 configured to secure the restriction element 8 in place on a user's limb. Such a fastening element may prevent removal of the restriction element 8 from the user's limb without release of the fastening element 9. The fastening element 9 comprises a press stud 11 which may be secured to its corresponding fastening 11A so as to secure the fastening element 9 around a user's limb. Any other suitable fastening element which is capable of securing the restriction element 8 to the user's limb may be used.

The restriction element may, for example, be filled with small plastic pellets of at least one of polystyrene, polypropylene or polyethylene. Alternatively or in addition, the restriction element 8 may be filled with a hollow fibre filling, for example made from polyester. The restriction element 8 may be washable. Similarly, the restriction element 8 may be inflatable. The restriction element 8 not only acts to restrain the user's hand within the device, as will become clearer with reference to later Figures, but also may act as a cushion for the user's wrist within the shielding member 4.

The device 2 further comprises a closure member 10. The interaction between the shielding member 4, restriction element 8 and closure member 10 in use will be described in more detail below with reference to later Figures. As shown in FIG. 1 the closure member 10 comprises a threaded portion 12 which is configured to engage with a threaded portion 20 (shown in FIG. 2) on the shielding member 4. The threaded portions 12, 20 together provide a locking arrangement.

The closure member 10 comprises a cylindrical body 16 which is hollow except for a hand grip 14 which extends between outer walls of the cylindrical body 16. The hand grip 14 may be a separate component which is attached to the cylindrical body 16 by any suitable means. For example, the hand grip 14 may be secured in place by an adhesive. The hand grip 14 may be used in moving the closure member 10 relative to the shielding member 4. As will become clearer with reference to later Figures, the hand grip 14 may be dimensioned so as to prevent the user's hand from extending through the closure member 10.

At least part of the shielding member 4 and/or the closure member 10 may be made of a hard synthetic resin such as an amorphous thermoplastic (e.g. acrylic, polycarbonate, polyvinyl chloride (PVC), polystyrene, polypropylene, polyethylene terephthalate glycol). In addition, or alternatively, the shielding member 4 may be made from a rigid foam.

Figure 2:
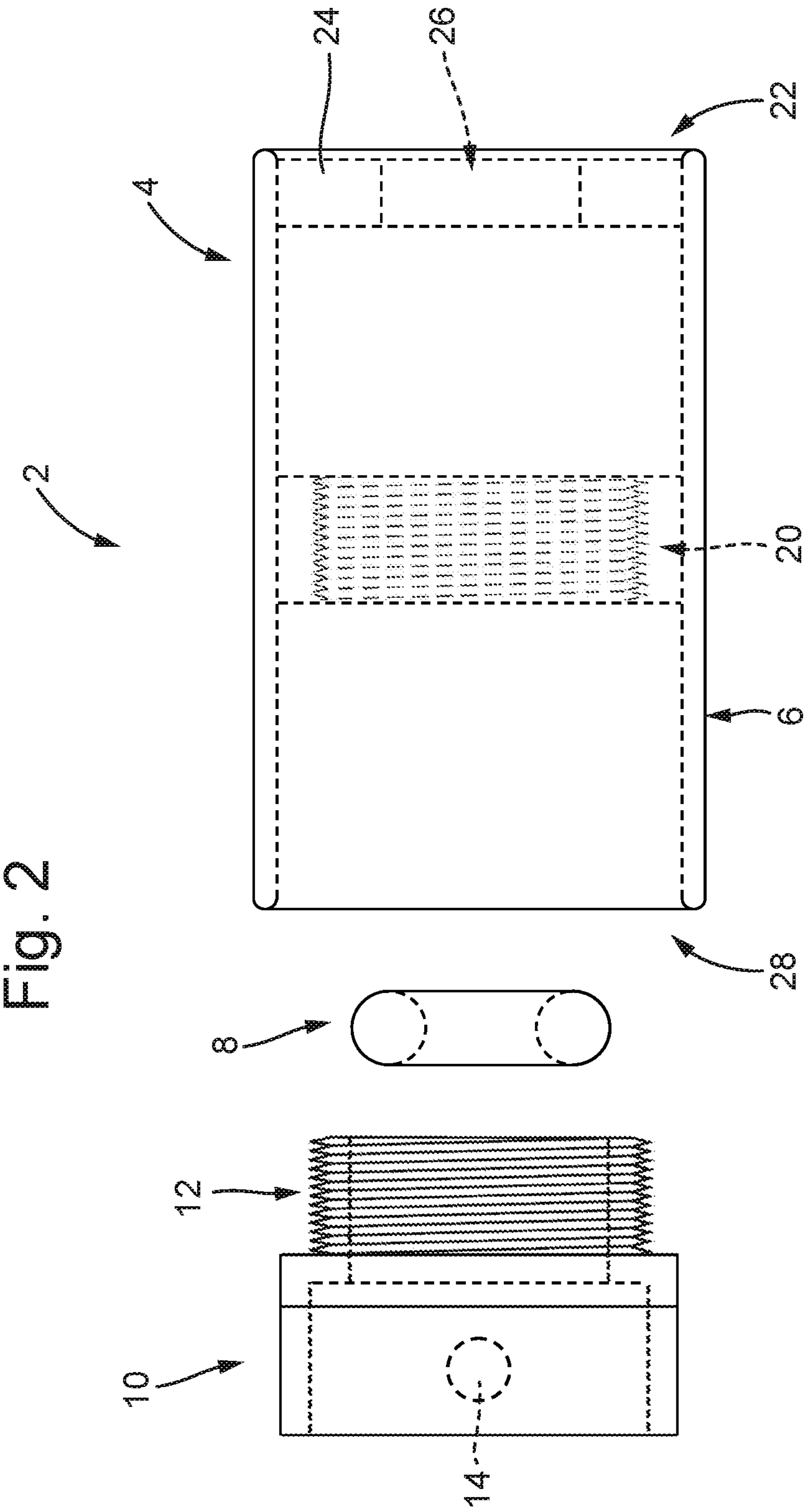
FIG. 2 is cross-sectional side view of the limb shielding device shown in FIG. 1.

FIG. 2 shows a cross-sectional side view of the device 2 shown in FIG. 1. As shown in this Figure, the shielding member 4 comprises an internal threaded portion 20. As previously mentioned, the threaded portion 12 on the closure member 10 and the threaded portion 20 on the shielding member 4 together form the locking arrangement which allows the closure member 10 to be held in a closed position.

The threaded portions 12, 20 each comprise at least half a rotation of thread and in the depicted embodiment comprise at least twelve full rotations of thread. Of course, any number of rotations may be provided, and the number of rotations may depend on the particular application of the device 2.

At the proximal end 22 of the shielding member 4, a ring shaped element 24 defines an opening 26 which is dimensioned to allow a user's limb to be inserted into the shielding member 4. The opening 26 may have a circular shape, however any suitable shaped may be used so long as it is capable of receiving the user's limb. The ring shaped element 24 may be a separate part which is attached to the cylindrical tube 6. For example, the ring shaped element 24 may be provided by a foam insert which may make the opening 26 more comfortable around a user's limb. Alternatively, the ring shaped element 24 may be integrally provided with the cylindrical tube 6.

The distal end 28 of the shielding member 4 is open and is dimensioned to receive the restriction element 8 and the closure member 10. The relative dimensions of the shielding member 4, restriction element 8 and closure member 10 are shown more clearly in FIG. 3.

Figure 3:
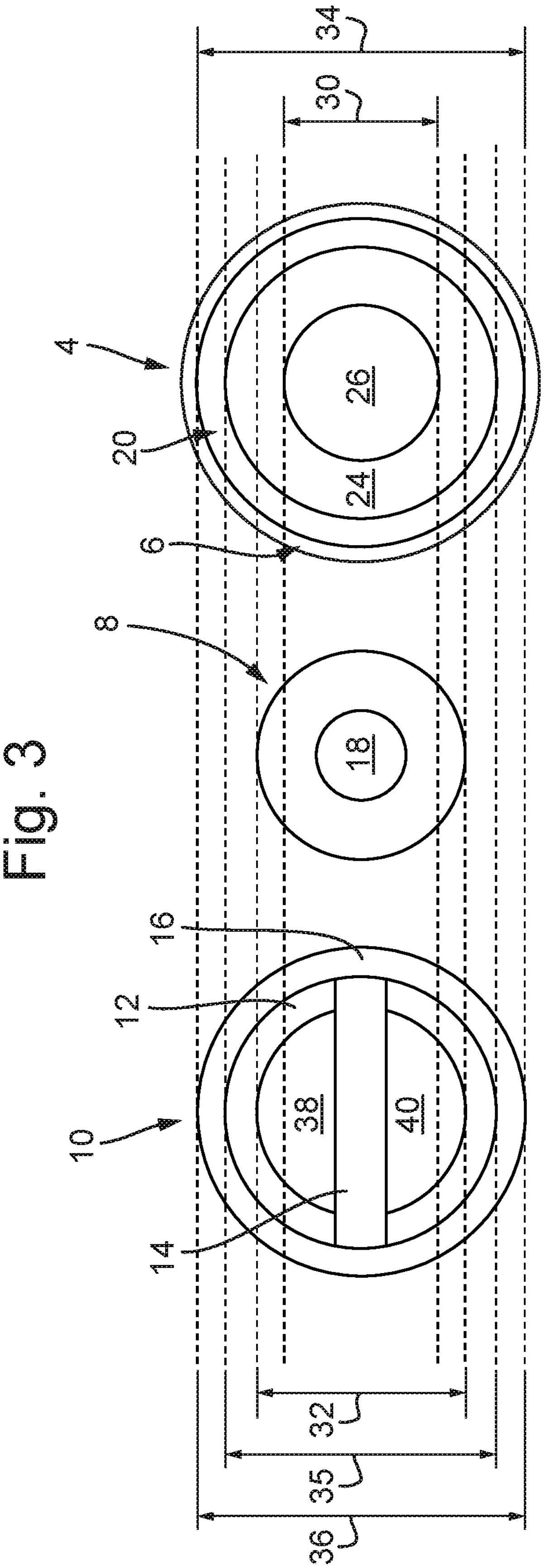
FIG. 3 is an end-on view of the components of the limb shielding device shown in FIG. 1.

FIG. 3 shows an end-on view of the shielding member 4, restriction element 8 and closure member 10. As shown, the internal diameter 30 of the opening 26 is less than the external diameter 32 of the restriction element 8, at least when the restriction element 8 is secured to a user's limb. Accordingly, at least when the restriction element 8 is attached to a user's limb, it will not be possible to pull the limb, with the restriction element 8 attached thereto, through the opening 26. Further, the cylindrical tube 6 and the closure member 10 are dimensioned such that the cylindrical tube 6 has an internal diameter 34 which is sufficient to receive the cylindrical body 16, of the closure member 10, which has a diameter 36. In other words, the diameter 36 of the cylindrical body 16 is less than or equal to the internal diameter 34 of the cylindrical tube 6. As a result of these relative dimensions, the closure member 10 can slide within the cylindrical tube 6. This will become more apparent with reference to later Figures. Additionally, as shown, the external diameter 32 of the restriction element 8 is less than the internal diameter 34 of the cylindrical tube 6 such that the restriction element 8 can fit within the cylindrical tube 6. Further, the external diameter 32 of the restriction element 8 is less than the internal diameter 35 of the threaded portion 20 such that the restriction element 8 can pass through the cylindrical tube 6 and pass the threaded portion 20, thereby allowing a user to fully retract their limb, with the restriction element 8 attached thereto, into the cylindrical tube 6.

As is also shown most clearly in FIG. 3, the hand grip 14 and cylindrical body 16, of the closure member 10, together define two vent apertures 38, 40. These vent apertures 38, 40, at least when the closure member 10 is secured to the shielding member 4, permit air flow into the shielding member 4. As discussed previously, this may improve the comfort for the user.

For the device 2 described above, the shielding member 4 has an entirely smooth, uninterrupted outer surface. This advantageously means that the shielding member 4 itself cannot be used, for example, for scratching. However, the shielding member 4 may be fenestrated so as to provide additional air circulation to the limb within the shielding member.

Figure 4A:
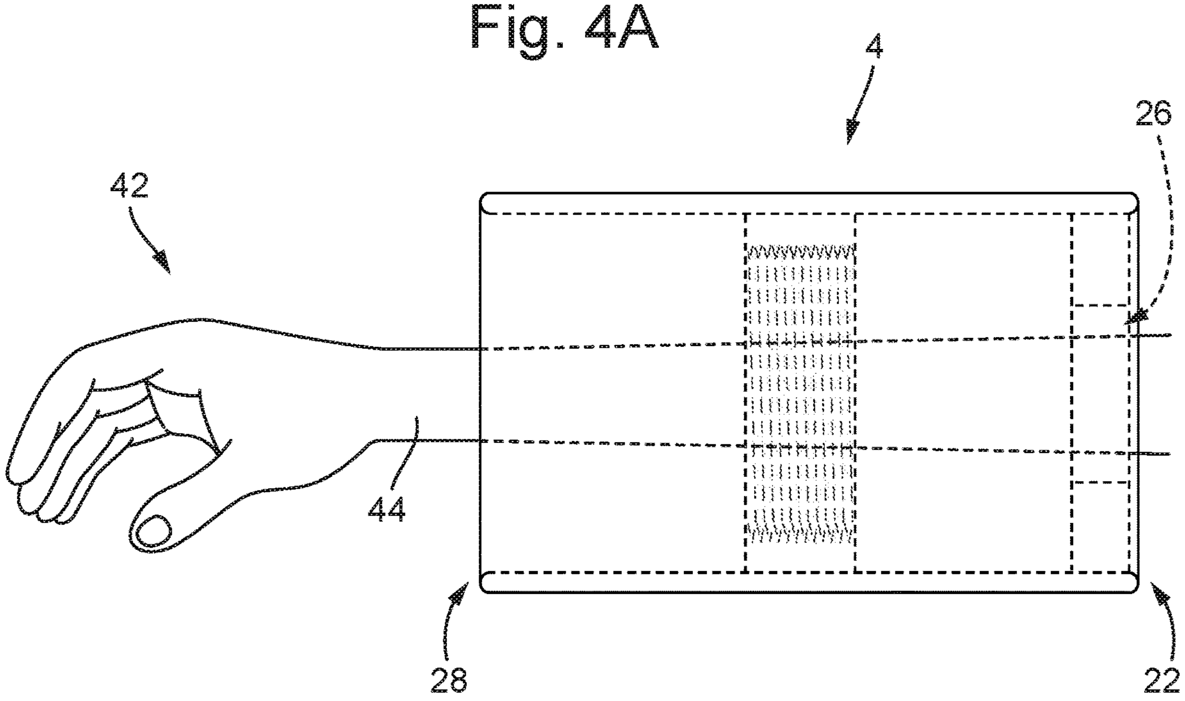
FIGS. 4A-4D are schematic views showing attachment of the limb shielding device shown in FIG. 1 to a user's hand and arm.

FIGS. 4A-4D illustrative sectional views of the attachment of the device 2 to a user's hand 42 and arm 44. The first step of the process is illustrated in FIG. 4A in which the user inserts their hand 42, and arm 44, through the opening 26 in the proximal end 22 of the shielding member 4, and continues to advance their hand 42 relative to the shielding member 4 until at least their hand 42 extends out of the distal end 28 of the shielding member 4.

Figure 4B:
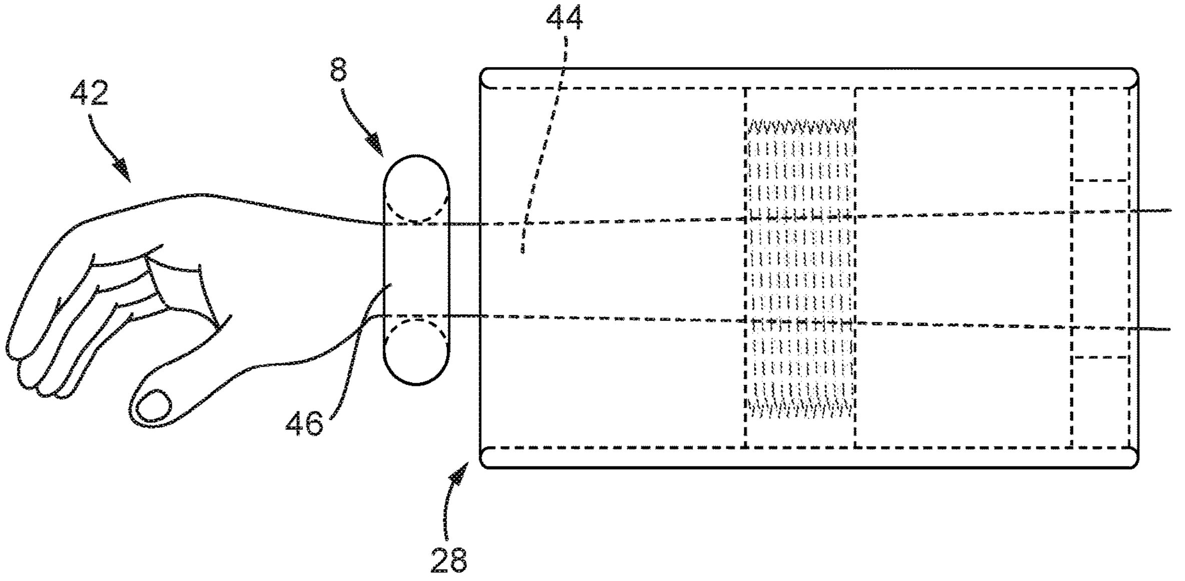

As shown in FIG. 4B, once the hand 42 is extending out of the shielding member 4, the user may then attach the restriction element 8 around their arm 44, specifically around their wrist 46. This may be achieved by pushing the user's hand 42 through the opening 18 in the restriction element 8, whilst holding the restriction element 8 with the user's other hand. A fastening element 9 (see FIG. 1) may then be fastened in place to secure the restriction element 8 to the user's wrist 46. Once the restriction element 8 is attached to the user's first wrist 46, the above process may be repeated on the user's other hand with a second device 2 such that both hands are in the configuration shown in FIG. 4B. By repeating the process at this stage, neither hand 42 is yet fully constrained within the shielding member 4, and thus the first hand 42 is free to assist in the application of a second device 2 to the user's other hand 42

Figure 4C:
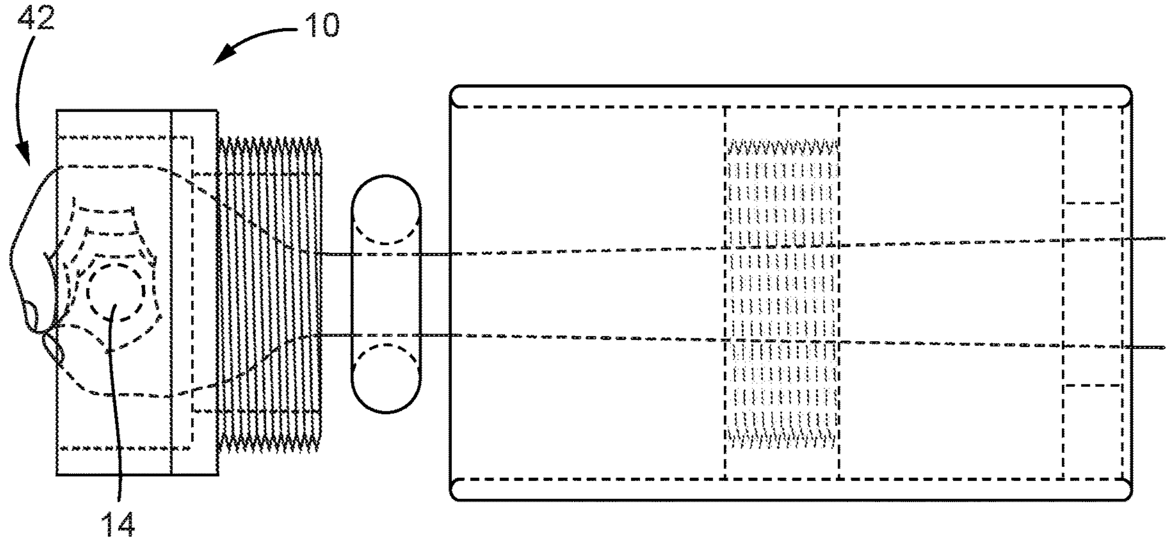
Figure 4D:
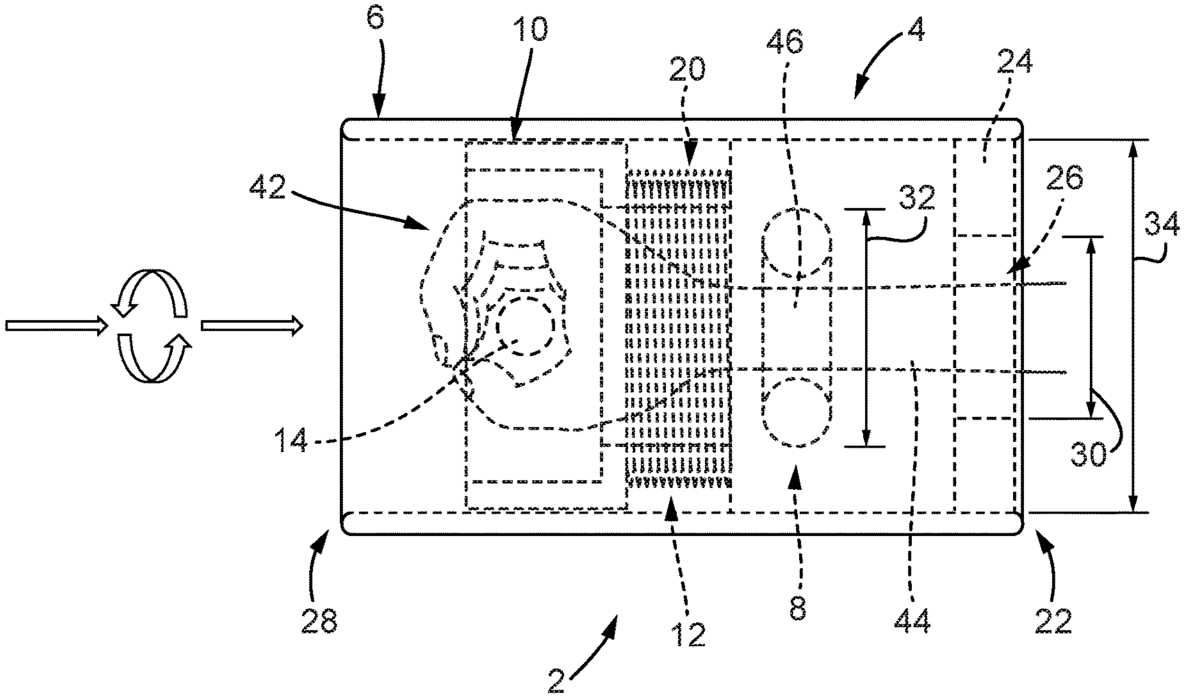

As illustrated in FIG. 4C, a user may then proceed to grab the hand grip 14, of the closure member 14, with their hand 42. As illustrated in FIG. 4D, the user may then retract their hand 42 backwards, whilst gripping the hand grip 14, such that the closure member 10 is brought into the inside of the cylindrical tube 6. The closure member 10 is thus capable of being moved, by the user's hand 42, into a closed position. As shown in FIG. 4D, when in the closed position, the user's hand 42, their wrist 46 and indeed part of their arm 44, e.g. at least part of the user's limb, is constrained within the shielding member 4. The closure member 10 may be pulled backwards to the point at which the threaded portions 12, 20 engage and rotated relative to the shielding member 4 such that the threaded portions 12, 20 engage with one another and hold the closure member 10 in a closed position. The threaded portions 12, 20, which together provide the locking arrangement, therefore secure the closure member 10 in the closed position. As shown in this Figure, the closure member 10, at least when in the closed position, may be contained within the cylindrical tube 6, i.e. an outer wall of the shielding member 4.

The steps described above for FIGS. 4C and 4D may be repeated by the user's second hand 42 on the second device 2. Accordingly, the device 2 may be attached to each hand 42 by a user themselves without requiring assistance from a third party.

As is apparent in FIG. 4D, the various components are configured such that the opening at the distal end 28 is sufficiently far removed from the extended fingers of the user's hand 42 thereby preventing the user from causing harm, for example to themselves. This may be achieved through appropriate dimensions of the tube 6, positioning of the threaded portion 20 in the tube 6 and also the relative dimensions of the closure member 10. The proximal end 22 of the tube 6 may be designed to sit anywhere on the arm 44 between the wrist and the elbow. The position of the tube 6 on the user's arm 44 may depend on how far the user has their hand 42 inserted into the device 2. The user 42 may freely move their hand 42 within the tube 6 longitudinally, for example by releasing the hand grip 14 and retracting their arm 44 backwards and forwards. The tube 6 may not extend over the elbow and may thereby allow flexing of the arm 44 at the elbow. Again, this may improve the comfort of the device 2 for the user.

As is most clearly visible in FIG. 4D, when the restriction element 8 is attached around the user's limb, e.g. around their wrist 46, the outer dimension 32 of the restriction element 8 is greater than the internal dimension 30 of the opening 26, which is defined by the ring shaped element 24. Accordingly, the restriction element 8 effectively restricts the opening 30 relative to the user's limb, i.e. it provides a means for restricting the opening 26 relative to the user's wrist 46, i.e. their limb. Therefore, once the arm 46 is inserted and the opening 26 is restricted relative to the user's wrist 46, the wrist 46 cannot be retracted through the opening 26. As is also shown, the outer dimension 32 of the restriction element 8 is less than the internal diameter 34 of the cylindrical tube 6. Accordingly, the restriction element 8 when attached to the wrist 46 may be free to move within the shielding member 4. Through appropriate sizing of the restriction element 8, the position of the closure member 10 in the closed position and the size of the cylindrical tube 6, it may be possible to allow the restriction element 8 to move longitudinally and laterally within the shielding member 4, as well as being able to rotate relative to the shielding member 4. As discussed previously, this freedom of movement may significantly increase the comfort of the device 2 for the user, which may increase the likelihood of a user wearing the device 2 and may potentially increase the amount of time for which they wear the device 2.

Whilst it has been described above that a device 2 may be attached to each of a user's hands 42, of course, if it is only desired to apply the device 2 to one hand 42, then the user need not necessarily repeat the steps above on the second hand 42.

The device 2 described above may also be detached by the user as well as attached. In order to remove the shielding device 2, the user may perform the reverse of the steps described above in FIGS. 4A-4D. With the device 2 in the configuration shown in FIG. 4D, the user may perform a predetermined operation, in this instance in the form of rotation of the closure member 10 relative to the shielding member 4, thereby releasing the locking arrangement provided by the threaded portions 12, 20. When rotating the closure member 10 relative to the shielding member 4, it may be necessary to hold the shielding member 4 in a fixed position. This may, for example, be achieved by holding the shielding member 4 between a user's knees, or by resting the shielding member 4 against a surface, e.g. worktop. The threaded portions 12, 20 comprise a number of turns of thread, and thus a user will have to rotate the closure member 10 through a number of full rotations before they are able to release the threaded portions 12, 20. The number of rotations required to release the closure member 10 may prevent a user from, for example, accidentally or subconsciously removing the shielding device.

Once the closure member 10 has been rotated by a sufficient amount, the threaded portions 12, 20 will become disengaged and the user may push the closure member 10 out of the shielding member 4 with their hand 42, thereby moving the closure member 10 from a closed position seen in FIG. 4D towards an open position as seen in FIG. 4C.

The user may then proceed to repeat the above for their second hand 42 in order to move the closure member 10 into an open position. Following this, the user may then remove the restriction element 8 from each of their wrists 46 and subsequently retract their hand 42 back through the opening 26 in the device 2.

Whilst the above is described as having a locking arrangement which requires sustained effort from a user in order to release the locking arrangement, it may be desirable for the user to more easily release the locking arrangement. In this case, the locking arrangement may more easily be overcome. For example, the closure member 10 may instead be held in a closed position by an interference fit, rather than the threaded portions 12, 20. Such an interference fit may more easily be released by the user's hand 42.

Several variations of the limb shielding device 2 shown in FIG. 1 will now be described. Except for the variations that are described, the limb shielding device 2 has the same construction as shown in FIG. 1 and described above. Thus, like reference numerals refer to like parts and description thereof is not repeated. The different variations described below may be applied together in any combination.

Figure 5A:
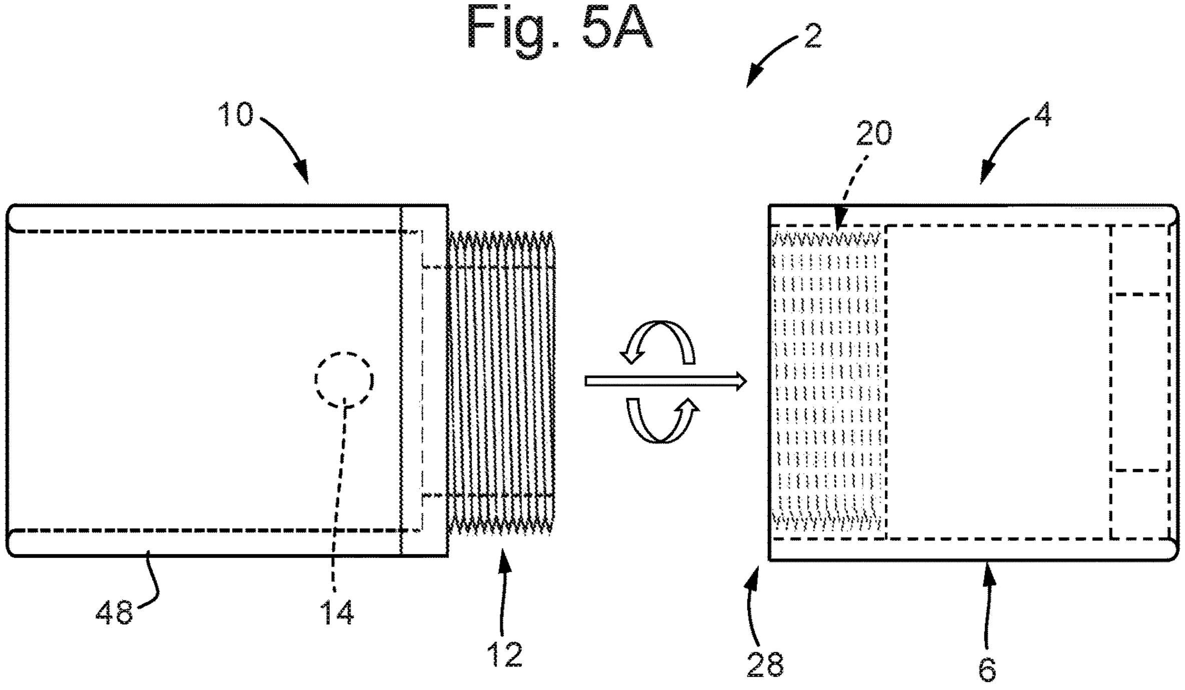
FIGS. 5A and 5B are cross-sectional side views showing a variation of the limb shielding device shown in FIG. 1.
Figure 5B:
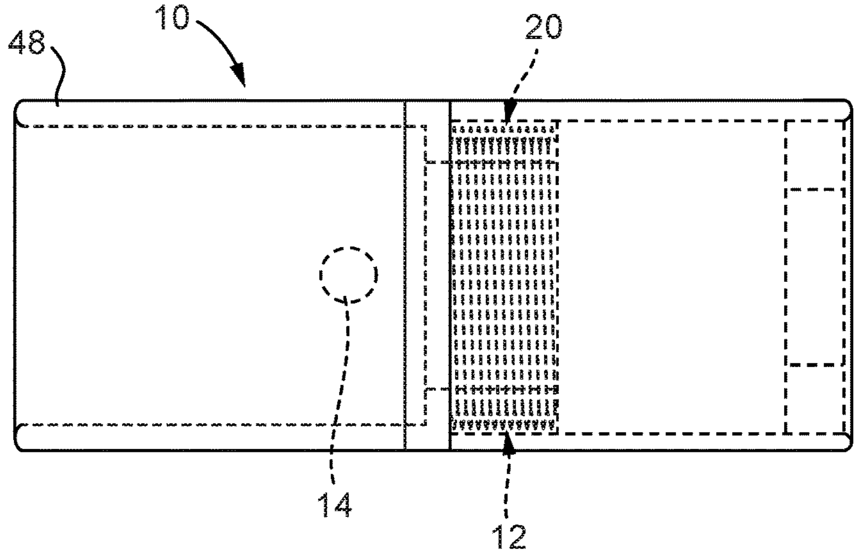

FIGS. 5A and 5B show a variation on the device 2 seen in earlier Figures. In this variation, the threaded portion 20 is arranged at the distal end 28 of the cylindrical tube 6 of the shielding member 20. The closure member 10 is also dimensioned such that its outside dimension matches that of the cylindrical tube 6. Accordingly, when the closure member 10 is in a closed position to close the shielding member 4, as shown in FIG. 5B, and when the threaded portions 12, 20 are engaged, the closure member 10 abuts against the distal end 28 of the cylindrical tube 6. Accordingly, the closure member 10 does not slide within the cylindrical tube 6 as is the case for the device 2 shown in FIG. 1. In this variation, to account for the fact that the closure member 10 does not sit within the cylindrical tube 6, the closure member 10 comprises a forward extending shield portion 48. When the closure member 10 is in the closed position shown in FIG. 5B, the user's fingers may be able to extend past the hand grip 14. Accordingly, the forward extending shield portion 48 serves to shield the fingers and thus prevent the user from being able to use their fingers, for example, to scratch themselves.

For any of the devices 2 described above, a further locking arrangement may be provided which can only be operated from outside the shielding member 4. For example, a strap with snap fasteners may be connected between the closure member 10 and the shielding member 4 and act to prevent relative rotation of the closure member 10 and the shielding member 4. Alternatively, a wedge may be inserted between the closure member 10 and the inside walls of the shielding member 4 so as to prevent relative rotation of the closure member 10 and shielding member 4. Such a further locking arrangement would need to be released by a third party before the user can release the locking arrangement provided by the threaded portions 12, 20.

Figure 6A:
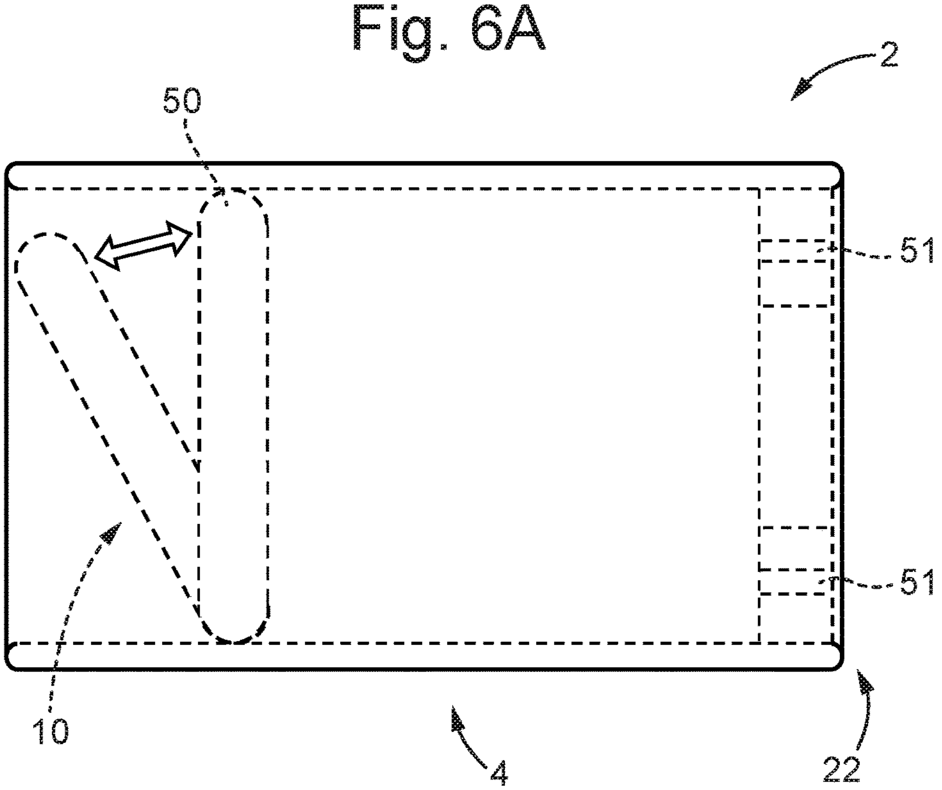
FIGS. 6A and 6B are cross sectional views showing another variation of the limb shielding device shown in FIG. 1.
Figure 6B:
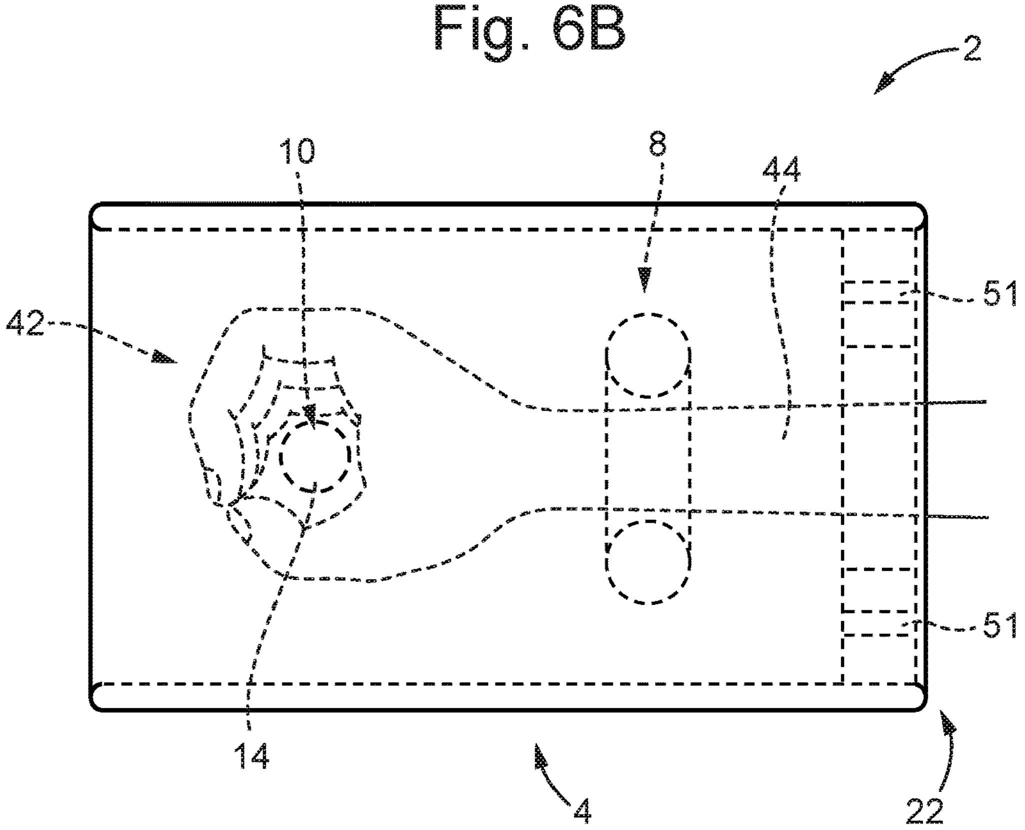

FIGS. 6A and 6B show another variation on the device 2 seen in earlier Figures. In this variation, instead of a separate closure member, the closure member 10 is pivotally mounted to the shielding member 4. As shown in FIG. 6B, when the user has inserted their hand 42 into the shielding member 4, and attached the restriction element 8, they may then grab the closure member 10 which is shown in the form of a hand grip 14 and pull it into a closed position as shown by the dashed line 50 in FIG. 6A. Once in this closed position, the user's hand 42 may be constrained within the device 2. The closure member 10 may comprise a snap fit arrangement at one end thereof for engaging with the shielding member 4 so as to secure the closure member 10 in the closed position.

In addition, the variation shown in FIGS. 6A and 6B also includes a plurality of vent apertures 51 at the proximal end 22 of the shielding member 4. As discussed previously, such vent apertures 51 may allow air to circulate into the inside of the shielding member 4, particularly around the portion of the shielding member 4 which extends around the user's arm 44, which may increase the comfort of the device 2.

Figure 7:
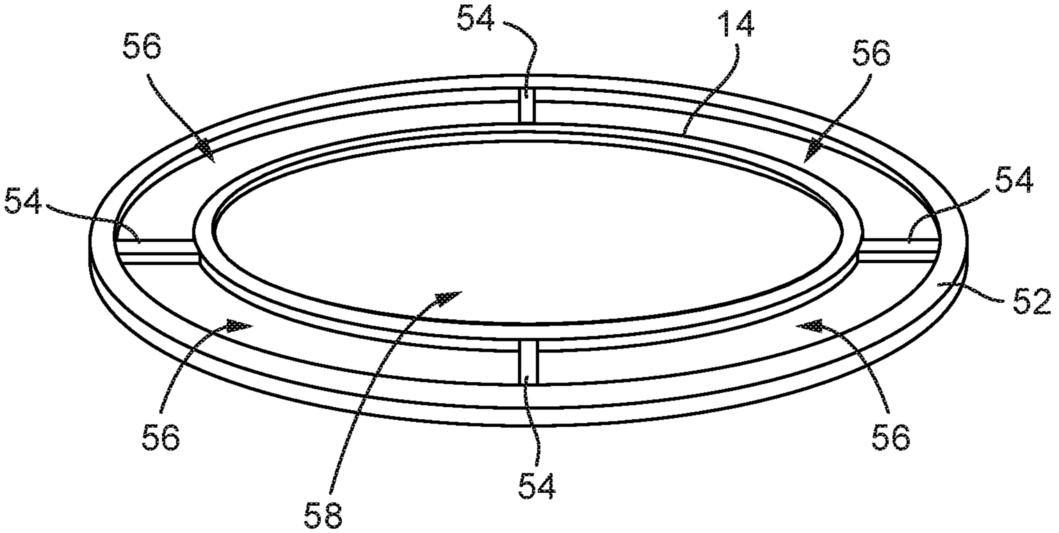
FIG. 7 is a perspective view of a variation of the hand grip of the limb shielding device shown in FIG. 1.

FIG. 7 shows a perspective view of a variation of the hand grip 14 of the closure member 10. Instead of the hand grip 14 being provided by a bar as shown, for example, in FIG. 1, the hand grip 14 may be ring shaped as shown in FIG. 7. The ring shaped hang grip 14 may be connected to an outer ring 52 by a plurality of supporting members 54. The hand grip 14, outer ring 52 and plurality of supporting members 54 together define a plurality of openings 56. The ring shaped hand grip 14 also defines a central opening 58. The arrangement shown in FIG. 7 may replace the hand grip 14 of the closure member shown in FIG. 1. When a user wishes to move the closure member 10, they may grab the hand grip 14 by passing at least one of their fingers through one of the plurality of openings 56 and one of their fingers through the central opening 58 thereby allowing them to grab the hand grip 14. The user may then pull the closure member 10, and rotate it accordingly. Alternatively, the user may pass two or more fingers through the openings 56, without passing any fingers through the central opening 58, when operating the closure member 10. The openings 56, 58 may be dimensioned such that the user's hand 42 cannot pass therethrough, and thus the arrangement shown in FIG. 7 may contribute towards constraining the user's hand within the device 2. The openings 56 and central opening 58 may also provide vent apertures that allow air to pass into the shielding member 4. The ring shaped element 24 shown in FIG. 2 may also have a similar construction to element shown in FIG. 7, however in this case the opening 58 would need to be sufficiently large to allow the user's limb to be inserted into the device 2.

Figure 8:
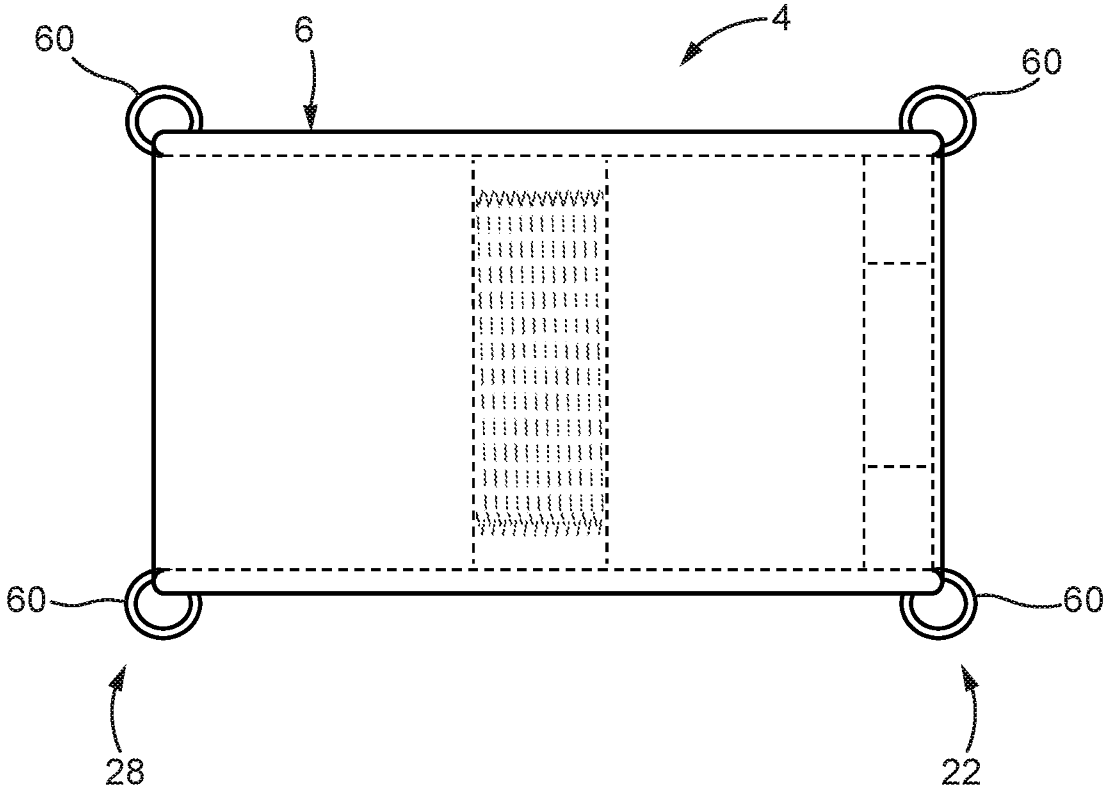
FIG. 8 is a cross-sectional side view of a variation of the shielding member of the limb shielding device shown in FIG. 1.

FIG. 8 shows cross-sectional side view of another variation of shielding member 4 shown in FIG. 1. In this variation, the cylindrical tube 6 of the shielding member 4 is formed of a sheet of material and comprises a rounded covering 60 arranged at the proximal end 22 and distal end 28 of the shielding member 4. In this variation, the rounded covering 60 is a separate element which is attached to the cylindrical tube 6. The rounded covering 60 may, for example, be provided by a smooth toroidal covering. Alternatively, the proximal end 22 and distal end 28 of the cylindrical tube 6 may be rounded through appropriate moulding. The rounded covering 60 may serve to blunt the proximal end 22 and distal end 28 of the shielding member 4 thereby potentially improving comfort for the user and also potentially preventing the shielding member 4 from being used as a scratching means.

Figure 9A:
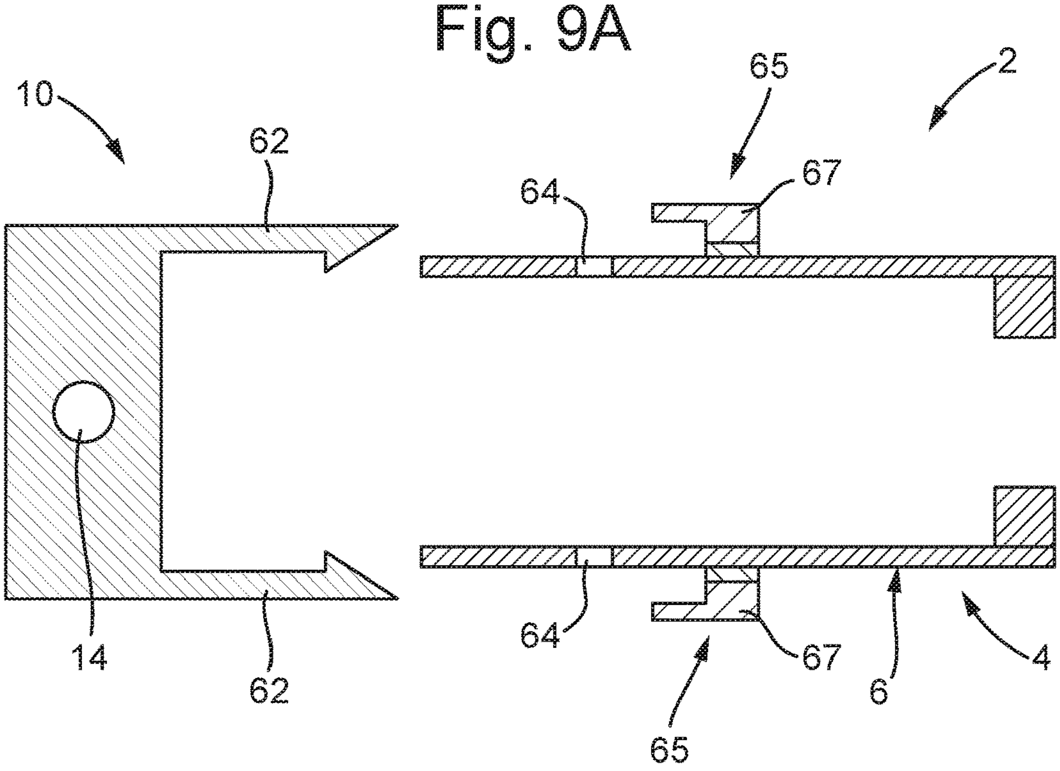
FIGS. 9A and 9B are cross-sectional side views of a variation of the shielding member of the limb shielding device shown in FIG. 1 comprising an alternative locking arrangement.
Figure 9B:
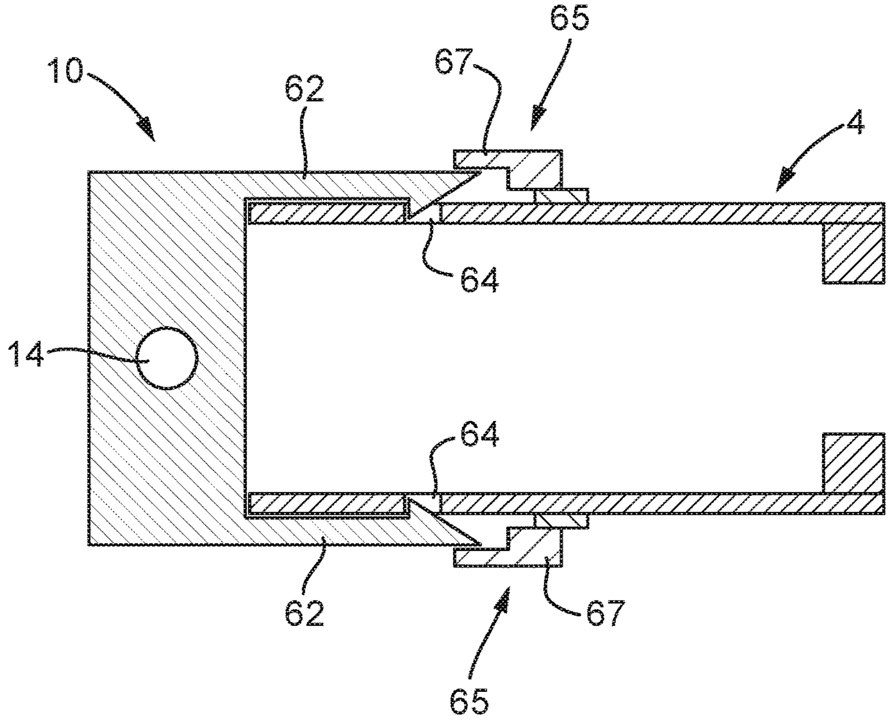

FIG. 9A shows a cross-sectional side view of a variation of the device 2 seen in FIG. 1. Instead of threaded portions 12, 20, the closure member 10 comprises snap-fit members 62 and the shielding member 4, specifically the cylindrical tube 6, comprises openings 64 for receiving the snap fit member 62. The snap fit members 62 and the openings 64 together provide a locking arrangement. As shown in FIG. 9B, the closure member 10 may be moved into a closed position in which the snap-fit members 62 engage with the openings 64. As the closure member 10 is moved into the closed position shown in FIG. 9B, the snap fit member 62 may be caused to deform slightly as they are forced to expand around the cylindrical tube 6. Accordingly, due to this deformation, when the snap fit members 62 engage with the openings 64, the snap fit members 62 will hold in place in the openings 64.

When the user's hand is constrained within the shielding member 4, the user may release the locking arrangement by pressing the snap-fit member 62 from within the shielding member 4 such that they release from the openings 64. The user may then push the closure member 10 out of the closed position, e.g. by pushing on the hand grip 14. The presence of multiple snap-fit members 62 may thus require a predetermined operation by the user which comprises operation of the multiple snap-fit members 62, before they can release the closure member 10. This may thus provide a barrier to removal. Any suitable snap-fit arrangement may be provided. Any suitable snap fit arrangement may be used, for example a cantilever, torsional or annular snap fit.

The device shown in FIGS. 9A and 9B comprises a further locking arrangement 65 which may be operated from outside the shielding member 4, e.g. by a caregiver. The further locking arrangement 65 comprises a slider 67 which is arranged to slide longitudinally with respect to the cylindrical tube 6. When the closure member is in the closed position as seen in FIG. 9B, and the snap fit members 62 are located in the opening 64, the slider 67 of the locking arrangement 65 may be moved such that it overlaps, or even engages with, the snap fit members 62. Accordingly, the slider 67 may thus prevent the snap fit member 62 from being pushed radially outwards, thereby preventing release of the closure member 10. The further locking arrangement 65 may, for example, be operated by a third party such as a caregiver who requires a level of control over when the user is able to remove the device 2. The arrangement shown in FIGS. 9A and 9B is just one example of a possible further locking arrangement 65 and any other suitable further locking arrangement may be employed.

Figure 10:
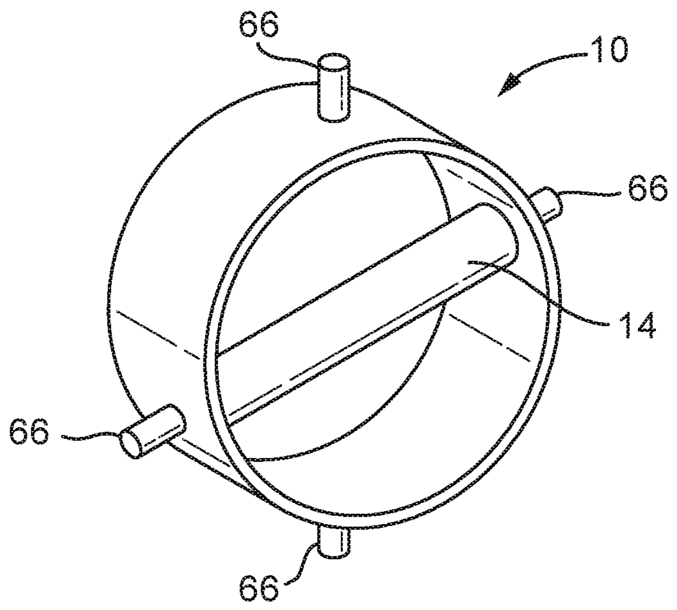
FIG. 10 is a perspective view of a variation of the closure member of the shielding member of the limb shielding device shown in FIG. 1.
Figure 11:
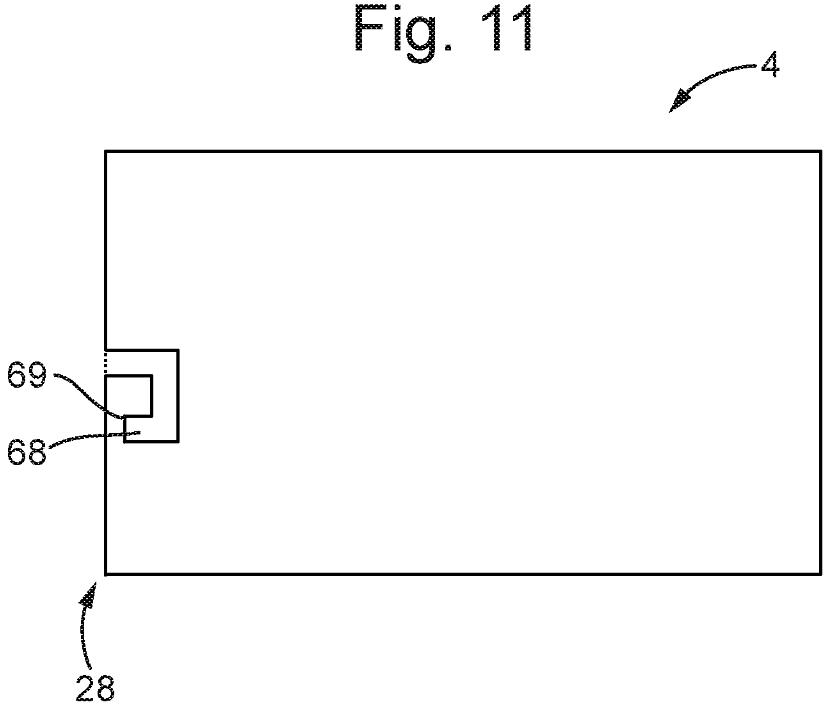
FIG. 11 is a perspective view of a variation of the shielding member for use with the closure member shown in FIG. 10.

FIG. 10 shows a perspective view of another variation of the closure member 10. In this variation, the closure member 10 comprises a plurality, in this case four, of radially extending elements 66. FIG. 11 shows a side view of a variation of the shielding member 4 designed for use with the closure member 10 shown in FIG. 10. The shielding member 4 comprises a plurality of slots 68 arranged at a distal end 28 thereof. The slots 68 need not necessarily be located at the distal end 28 of the shielding member 4. Instead, the slots 68 may be located within the shielding member 4, for example at a position corresponding to the position of the threaded portion 20 seen in FIG. 2. In this case, whilst not shown, the shielding member 4 comprises four slots.

With reference to FIG. 10 and FIG. 11, the plurality of radially extending elements 66 and the slots 68 together form the locking arrangement. A user may move the closure member 10 towards the shielding member 4 and engage each of the radially extending members 66 in a respective one of the slots 68. A user may then manipulate the closure member 10 such that the radially extending elements 66 are moved towards an end 69 of the slots 68. Once in position, this may correspond to a locked position. Due to the relatively complicated shape of the slots 68, a user will have to perform a relatively complicated movement of the closure member 10 in order to release the closure member 10 which comprises both rotational and longitudinal movement of the closure member 10. This relatively complicated movement may thus constitute a predetermined operation by the user. The slots 68 may, of course, have any suitable shape. The arrangement shown in FIGS. 10 and 11 effectively forms a bayonet-type fitting. Whilst not shown, the device in FIGS. 10 and 11 may further comprise at least one resilient member, e.g. in the form of a spring, which may act to provide a force holding the radially extending elements 66 at the end 69 of the slots 68. In this instance, a user would also have to overcome the force of the resilient member before being able to release the closure member 10 thereby further contributing towards the predetermined operation.

Figure 12:
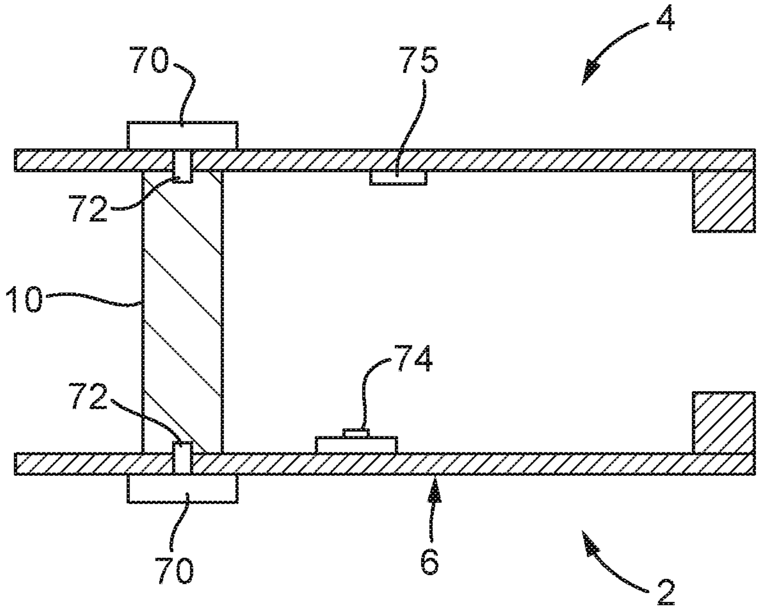
FIG. 12 is a cross sectional view of a variation of the locking arrangement of the shielding member of the limb shielding device shown in FIG. 1.

As an alternative to those discussed above, the locking arrangement may comprise a Storz connector which comprises a series of interlocking hooks and flanges. FIG. 12 shows a cross-sectional side view of another variation in which the locking arrangement comprises an electromagnetic locking arrangement 70. In this variation, the electromagnetic locking arrangement 70 is arranged to drive two bolts 72 into the closure member 10 so as to secure the closure member 10 in a closed position. The bolts 72 extends through the cylindrical tube 6 and into the closure member 10. A switch 74 may be arranged on an inside of the shielding member 4 for operation by a user to operate the electromagnetic locking arrangement 70. The switch 74 may require sustained effort by the user in order to operate the electromagnetic locking arrangement 70. For example, the switch 74 may comprise a number of different buttons which have to be pressed in a specific sequence in order to release the electromagnetic locking arrangement 70. Alternatively to that described above, the electromagnetic locking arrangement 70 may be connected to a voice controlled device and it may be possible for a user to operate the electromagnetic locking arrangement with their voice.

Additionally, in the variation shown in FIG. 12 the shielding member 4 comprises a means to determine the length of time the limb shielding device 2 has been worn by the user, in the form of a sensor 75. The length of time may be the amount of time the shielding device 2 has been worn continuously and/or the total time the shielding device 2 has been worn. The sensor 75 may be any suitable sensor, for example a heat sensor, opto-electronic sensor and/or an accelerometer. As mentioned previously, this sensor 75 may cooperate with another device so as to provide an alert to the user or a caregiver based on the amount of time the device 2 has been worn by the user.

Figure 13:
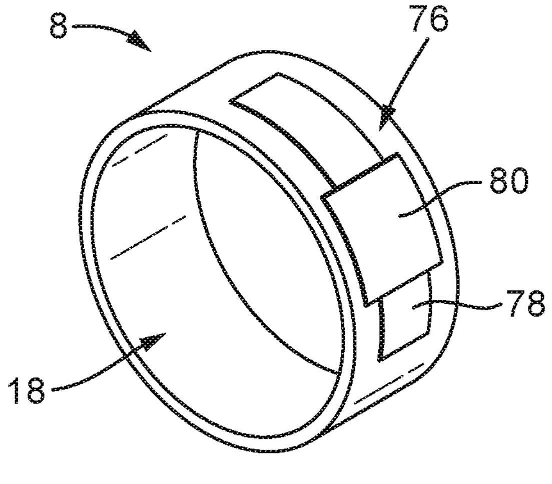
FIG. 13 is a perspective view of a variation of a restriction element having an adjustable size.

FIG. 13 shows a perspective view of a variation of the restriction element 8 shown in FIG. 1. In this variation, the restriction element 8 comprises an adjustment mechanism 76 which comprises a strap 78 and a buckle 80. The strap 78 may be pulled through the buckle 80 so as to adjust the size of the restriction element 8. This may, for example, allow the opening 18 to be reduced. This may make the restriction element 8 suitable for use by a number of different user's and/or allow the restriction element 8 to be used on a variety of different limbs. In addition or alternatively, the restriction element 8 may comprise a Velcro strap for achieving adjustment of the restriction element.

Figure 14A:
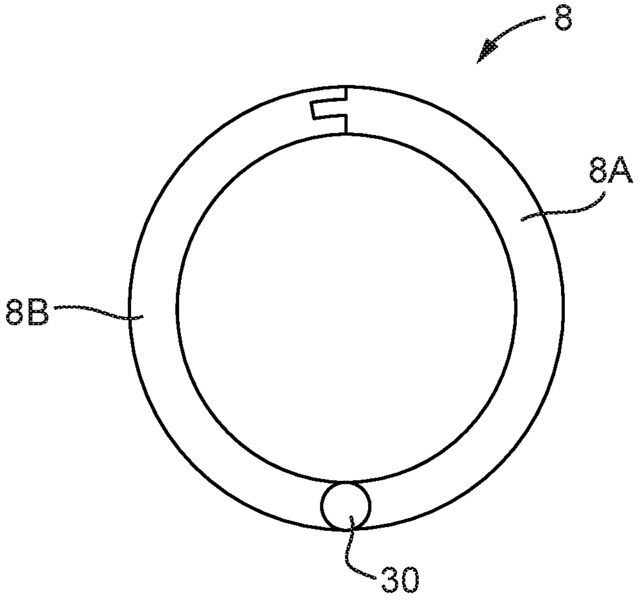
FIGS. 14A-14B are end-on views of another variation of a restriction element which is openable and closable.
Figure 14B:
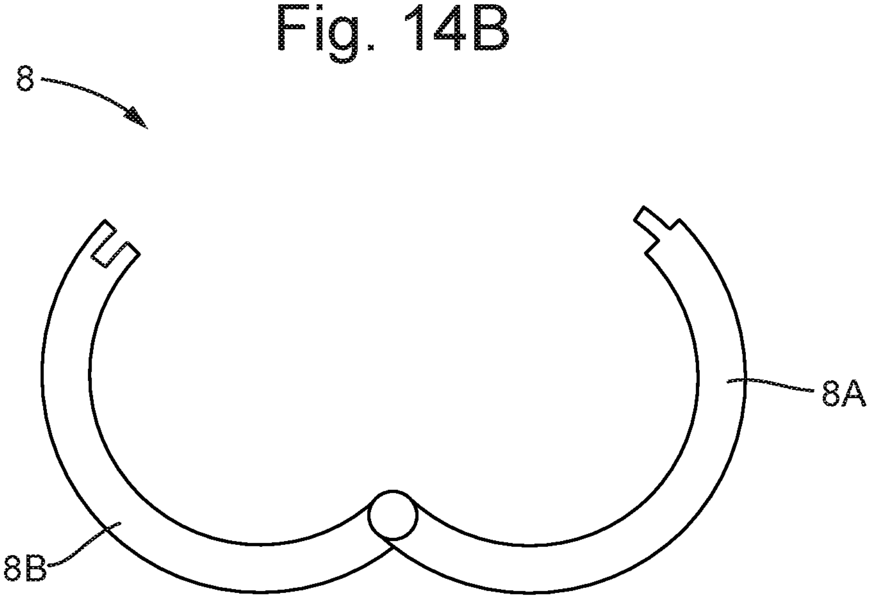

FIG. 14 shows an end-on view of another variation of the restriction element 8. In this variation, the restriction element 8 comprises two halves 8A, 8B, connected via a hinge 30. As shown in FIG. 14B, the hinge 30 allows the two halves 8A, 8B to be opened for receiving a user's limb. The two halves 8A, 8B may subsequently be closed for securing around the user's limb. This arrangement may advantageously make it easier for the user to insert their limb into the restriction element 8. The two halves 8A, 8B may be held together in a closed position, as seen in FIG. 14A, by any suitable means.

The restriction element 8 described above has a circular shape, however this is not essential and the restriction element 8 may have any other suitable shape, for example it may have an elliptical shape. It's shape may at least partially be defined by the shape of the shielding member 4. Whilst the restriction element 8 has been shown as enclosing a full circle, this is not necessary and depending on the specific dimensions of the user's limb and the opening 26 on the shielding member 4, the restriction element may instead only extend part way around a user's limb. For example, the restriction element may be in the form of a broken ring which extend 270° around a user's limb. Such a broken ring may make it easier for the user to attach the restriction element 8 to their limb.

Figure 15:
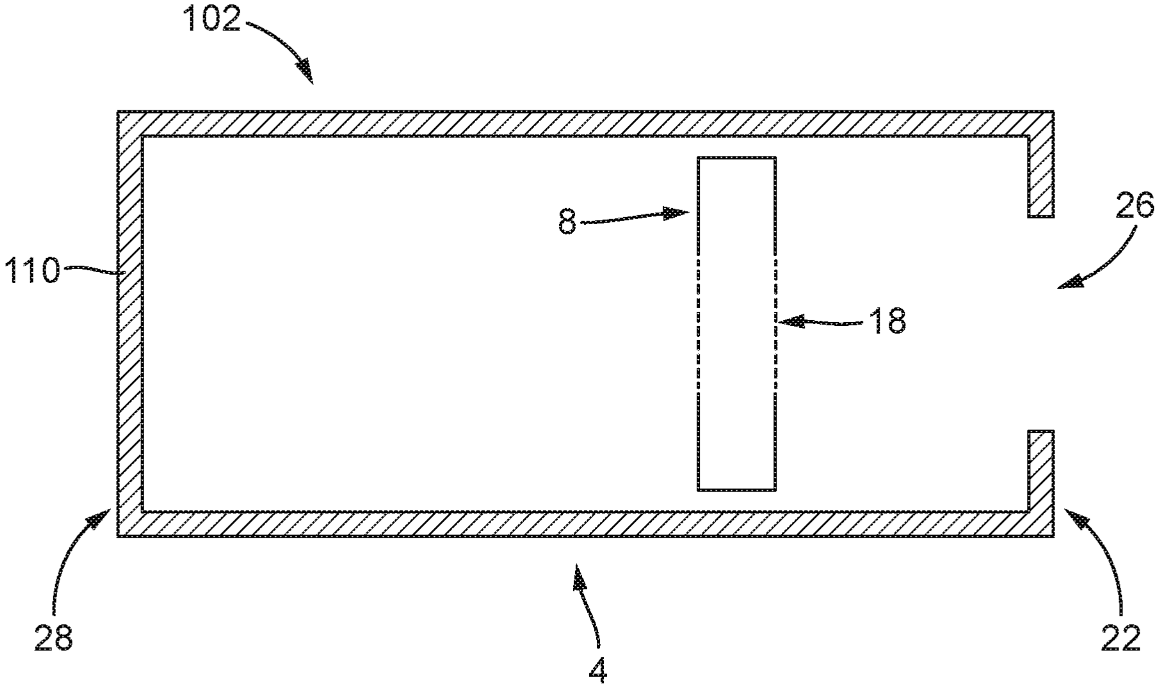
FIG. 15 shows a cross-sectional side view of another variation of a limb shielding device with a fixed closure member.

FIG. 15 shows a side cross-sectional side view of a limb shielding device 102. Similarly to the device 2 shown in FIG. 1, the device 102 comprises a shielding member 4 which comprises an opening 26 at a proximal end 22 thereof which is dimensioned to allow a user's limb to be inserted into the shielding member 4. The device 102 further comprises a restriction element 8, separate from the shielding member 4, configured to attach around a user's limb such that an outer dimension of the restriction element 8 is greater than the opening 26 such that user's limb cannot be retracted through the opening 26 and such that the restriction element 8 when attached to the limb may be moved within the shielding member 4.

The device 102 comprises a closure member 110 arranged at a distal end 28 of the shielding member 4 to permanently prevent a user's limb from passing through the distal end 28 of the device 102. The closure member 110 is integrally formed with the shielding member 4. In order to put on the device 102, a user may insert their limb into the shielding member 4 through the opening 26 and push their limb through the opening 18 in the restriction element 8. The restriction element 8 may be inflatable, and once the limb is inserted, the restriction element 8 may be inflated so as to grip around the limb within the device 102. Alternatively, the user may attach the restriction element 8 to their limb, insert their limb with the restriction element 8 attached through the opening 26, and subsequently inflate the restriction element 8 to constrain the limb within the device 102. At this point, the portion of the limb within the device 2 may then be constrained within the device 102 as the limb will be prevented from being retracted through the opening 26 due to the restriction element 8. The limb will also be prevented from passing through the distal end 28 of the device 102 due to the closure member 110. The restriction element 8 will nonetheless allow the limb to move within the shielding member 4, thus potentially increasing the comfort for the user.

Figure 16:
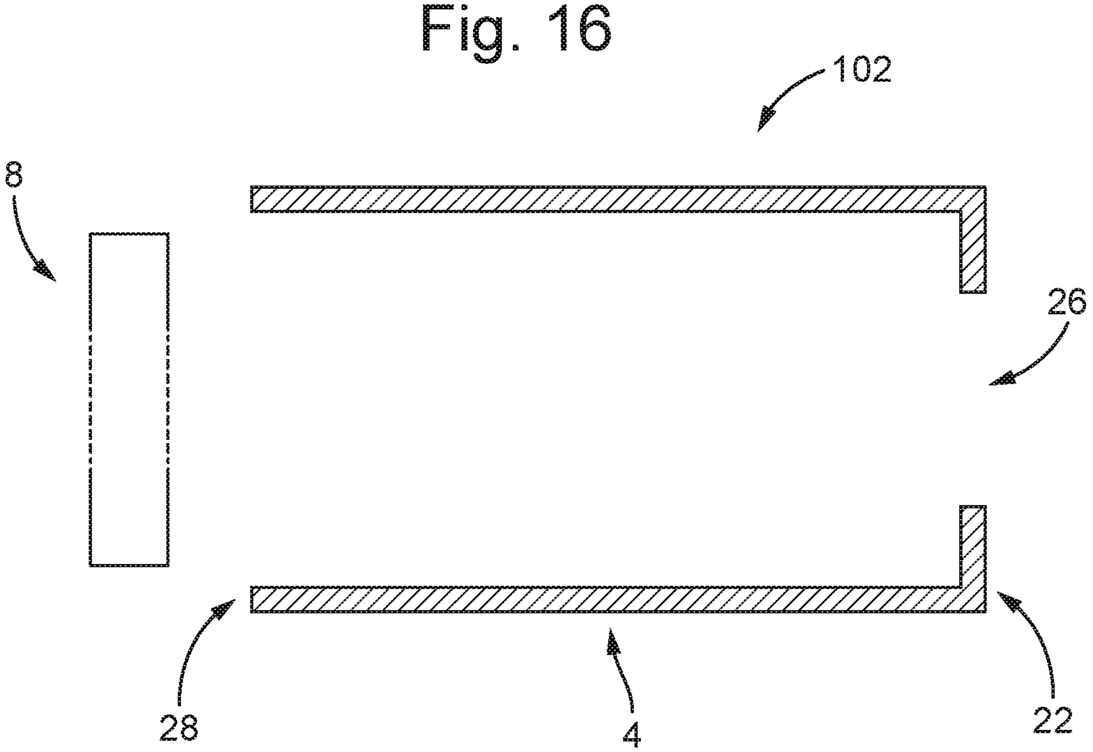
FIG. 16 shows a cross-sectional side view of another variation of a limb shielding device with no closure member.

The device 102 need not necessarily cover the entire limb or entirely constrain the limb within the device 102. Instead, a portion of the limb may be free to extend out of a distal end 28 of the device 102. A limb shielding device 102 of this type is shown in FIG. 16. The device 102 comprises a shielding member 4 with an opening 26 at a proximal end 22 thereof. The device 102 further comprises a restriction element 8. Unlike earlier variations, however, the device 102 does not comprise a closure member. Accordingly, a limb inserted within the device 102 and with the restriction element 8 attached will be prevented from being retracted through the opening 26, but may nonetheless be able to extend out of a distal end 28 of the shielding member 4. This may allow the user to protect a portion of their limb, allowing a degree of free movement of the shielding member 4 relative to the limb, whilst at the same time maintaining use of at least part of the limb, e.g. their hand extending through the distal end 28 of the device 102.

Figure 17:
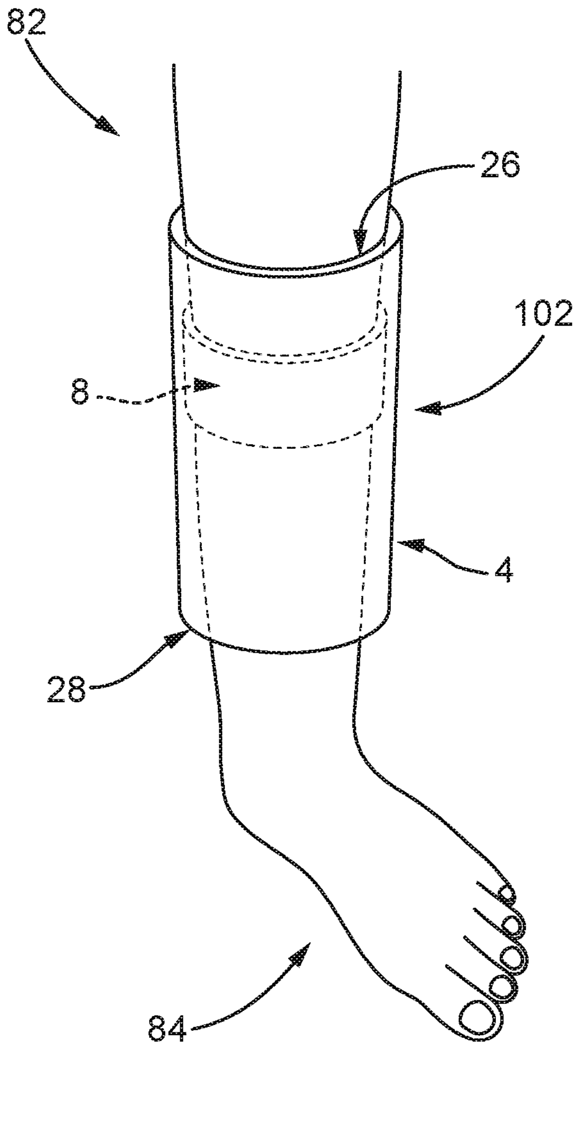
FIG. 17 shows a perspective view of the limb shielding device shown in FIG. 16 used in shielding a user's leg.

The device 102 of FIG. 16 is shown in use in FIG. 17 wherein the device 102 is used to shield a portion of a user's lower leg 82. As shown in this Figure, the foot 84, and indeed the lowermost portion of the user's leg 82, extends out of the distal end 28 of the device 102. Through the use of the restriction element 8, the shielding member 4 will be held on the user leg 82 and prevented from falling down, as the restriction element will not be able to fit through the opening 26. The shielding member 4 will nonetheless be free to move, at least partially, with respect to the user's leg 82. For example, the shielding member 4 may move upwards away from the restriction element 8, rotationally and/or laterally with respect to the user's leg. As previously described, this may increase the comfort of the device 2 for the user. As will be appreciated, the restriction element 8 may be dimensioned appropriately such that the shielding member 4 and restriction element 8 can be moved relative to one another.

The devices described above with respect to FIGS. 15, 16 and 17 may be used to shield any limb of a human or an animal. Any of the relevant features described above with respect to FIGS. 1-14 may also be applied to the devices described above with respect to FIGS. 15-17.

In any of the variations described above, at least the shielding member 4 may be transparent. As discussed previously, this may allow a user, or a caregiver to visually inspect the limb within the device 2.

The invention claimed is:

1. A limb shielding device, for shielding a user's hand, comprising:

a shielding member, configured to shield at least part of a user's limb, including the user's hand, comprising an opening arranged at a proximal end of the shielding member and dimensioned to allow a user's limb to be inserted into the shielding member;

a restriction element configured to restrict the opening relative to the user's limb such that once the user's limb is inserted and the opening is restricted relative to the user's limb, the user's limb cannot be retracted through the opening;

a closure member capable of being moved, by the user's hand within the shielding member, into a closed position such that at least part of the user's limb is constrained within the shielding member; and a locking arrangement for securing the closure member in the closed position, wherein the restriction element is configured to attach around a user's limb such that an outer dimension of the restriction element is greater than the opening, thereby restricting the opening relative to the user's limb.

2. A limb shielding device as claimed in claim 1, wherein the restriction element is separate from the shielding member and sized such that the restriction element, when attached to the user's limb, may be moved within the shielding member.

3. A limb shielding device as claimed in claim 2, wherein the restriction element has an adjustable size.

4. A limb shielding device as claimed in claim 2, wherein the restriction element is configured such that it can be opened for receiving a user's limb and closed for securing around the user's limb.

5. A limb shielding device as claimed in claim 2, wherein the restriction element is at least partially deformable.

6. A limb shielding device as claimed in claim 2, wherein the restriction element is inflatable.

7. A limb shielding device as claimed in claim 1, wherein the locking arrangement is configured to be capable of being released following a predetermined operation performed by the user's limb within the shielding member, and wherein the closure member is arranged such that it can be moved from the closed position to an open position by the user's limb within the shielding member.

8. A limb shielding device as claimed in claim 1, wherein the locking arrangement comprises a threaded portion on the closure member and a corresponding threaded portion on the shielding member for engagement with one another.

9. A limb shielding device as claimed in claim 8, wherein the threaded portion and corresponding threaded portion each comprise at least half a rotation of thread.

10. A limb shielding device as claimed in claim 1, wherein the locking arrangement comprises a snap fit arrangement configured to secure the closure member in the closed position.

11. A limb shielding device as claimed in claim 1, wherein the locking arrangement comprises at least one radially extending element on one of the closure member or shielding member and at least one female receiving portion, for receiving the radially extending element, on the other of the closure member or shielding member.

12. A limb shielding device as claimed in claim 1, wherein the locking arrangement comprises an electromagnetic locking arrangement.

13. A limb shielding device as claimed in claim 1, wherein the closure member is pivotally mounted to the shielding member.

14. A limb shielding device as claimed in claim 1, wherein the closure member comprises a hand grip for use in moving the closure member relative to the shielding member.

15. A limb shielding device as claimed in claim 1, wherein the closure member, at least when in the closed position, is contained within an outer wall of the shielding member.

16. A limb shielding device according to claim 1, wherein the closure member defines at least one aperture extending through the closure member.

17. A limb shielding device according to claim 1, further comprising a vent aperture at the proximal end of the shielding member.

18. A limb shielding device according to claim 1, wherein at least the shielding member is transparent, is formed of a sheet of material which comprises rounded proximal and distal ends, or is formed from an at least semi-rigid material.

19. A limb shielding device comprising:

a shielding member, configured to shield at least part of a user's limb, comprising an opening dimensioned to allow a user's limb to be inserted into the shielding member; and a restriction element, separate from the shielding member, configured to attach around a user's limb such that an outer dimension of the restriction element is greater than the opening, so that user's limb cannot be retracted through the opening and such that the restriction element when attached to the user's limb may be moved within the shielding member.

20. A limb shielding device as claimed in claim 19, further comprising a closure member arranged to permanently prevent a user's limb from passing through a distal end of the device.

* * * * *